United States Patent
Ho et al.

(10) Patent No.: US 7,060,095 B2
(45) Date of Patent: Jun. 13, 2006

(54) SUPPLEMENTARY ENDO-CAPSULAR LENS AND METHOD OF IMPLANTATION

(75) Inventors: Arthur Ho, Randwick (AU); Paul Erickson, Maroubra (AU); Fabrice Manns, Coral Gables, FL (US); Jean-Marie Parel, Miami Shores, FL (US)

(73) Assignee: Unisearch Limited, Sydney (AU)

( * ) Notice: Subject to any disclaimer, the term of this patent is extended or adjusted under 35 U.S.C. 154(b) by 386 days.

(21) Appl. No.: 10/275,496

(22) PCT Filed: May 8, 2001

(86) PCT No.: PCT/US01/14728

§ 371 (c)(1),
(2), (4) Date: Apr. 4, 2003

(87) PCT Pub. No.: WO01/85067

PCT Pub. Date: Nov. 15, 2001

(65) Prior Publication Data
US 2003/0208265 A1 Nov. 6, 2003

(51) Int. Cl.
*A61F 2/14* (2006.01)
(52) U.S. Cl. .................. 623/4.1; 623/6.12; 623/905; 523/107
(58) Field of Classification Search .............. 623/905, 623/6.11–6.56, 4.1; 523/107
See application file for complete search history.

(56) References Cited

U.S. PATENT DOCUMENTS

| | | | | | |
|---|---|---|---|---|---|
| 4,834,750 | A | * | 5/1989 | Gupta | 623/6.58 |
| 4,878,912 | A | * | 11/1989 | Castleman | 623/6.15 |
| 5,156,607 | A | * | 10/1992 | Kansas | 606/107 |
| 5,391,590 | A | * | 2/1995 | Gerace et al. | 523/107 |

(Continued)

FOREIGN PATENT DOCUMENTS

| WO | WO 89/00029 A1 | 1/1989 |
|---|---|---|
| WO | WO 93/03686 A3 | 3/1993 |

OTHER PUBLICATIONS

Nishi, O., and K. Nishi, "Accommodation Amplitude After Lens Refilling With Injectable Silicone by Sealing the Capsule With A Plug in Primates," *Archives of Ophthalmology*, Oct. 1998, pp. 1358-1361, vol. 116.

(Continued)

*Primary Examiner*—Suzette J-J Gherbi
(74) *Attorney, Agent, or Firm*—Kilpatrick Stockton LLP; David M. Krasnow

(57) ABSTRACT

The present invention is directed to a supplemental endo capsular lens (SECL) and the method of inserting and embedding the SECL within either a gel or polymer, inside the capsule of the crystalline lens, during phaco-ersatz or similar surgical procedures in order to supplement the refractive power of the eye with a view to (1) correcting ametropia while (2) maintaining a useable amplitude of accommodation.

62 Claims, 14 Drawing Sheets

U.S. PATENT DOCUMENTS

| | | | | |
|---|---|---|---|---|
| 5,984,916 A | * | 11/1999 | Lai | 606/11 |
| 6,048,364 A | | 4/2000 | Skottun | |
| 6,164,282 A | * | 12/2000 | Gwon et al. | 128/898 |
| 6,558,420 B1 | * | 5/2003 | Green | 623/6.34 |
| 6,598,606 B1 | * | 7/2003 | Terwee et al. | 128/898 |
| 6,692,526 B1 | * | 2/2004 | Snyder et al. | 623/6.63 |
| 6,720,314 B1 | * | 4/2004 | Melles | 514/150 |
| 2001/0051826 A1 | * | 12/2001 | Bogaert et al. | 623/6.23 |

OTHER PUBLICATIONS

Nishi, O., and Y. Sakka, "Anterior Capsule-Supported Intraocular Lens. A New Lens for Small-Incision Surgery and for Sealing the Capsular Opening," *Graefe's Archive for Clinical and Experimental Ophthalmology*, 1990, pp. 582-588, vol. 228, Springer-Verlag.

* cited by examiner

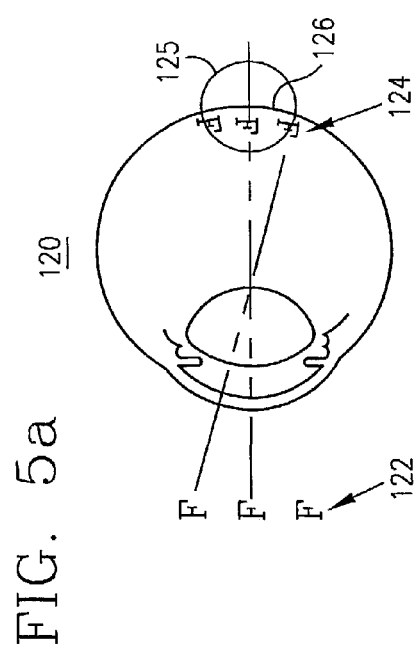

Effect of SECL on Accommodation and Refractive Correction in Two Types of Polymer Gel

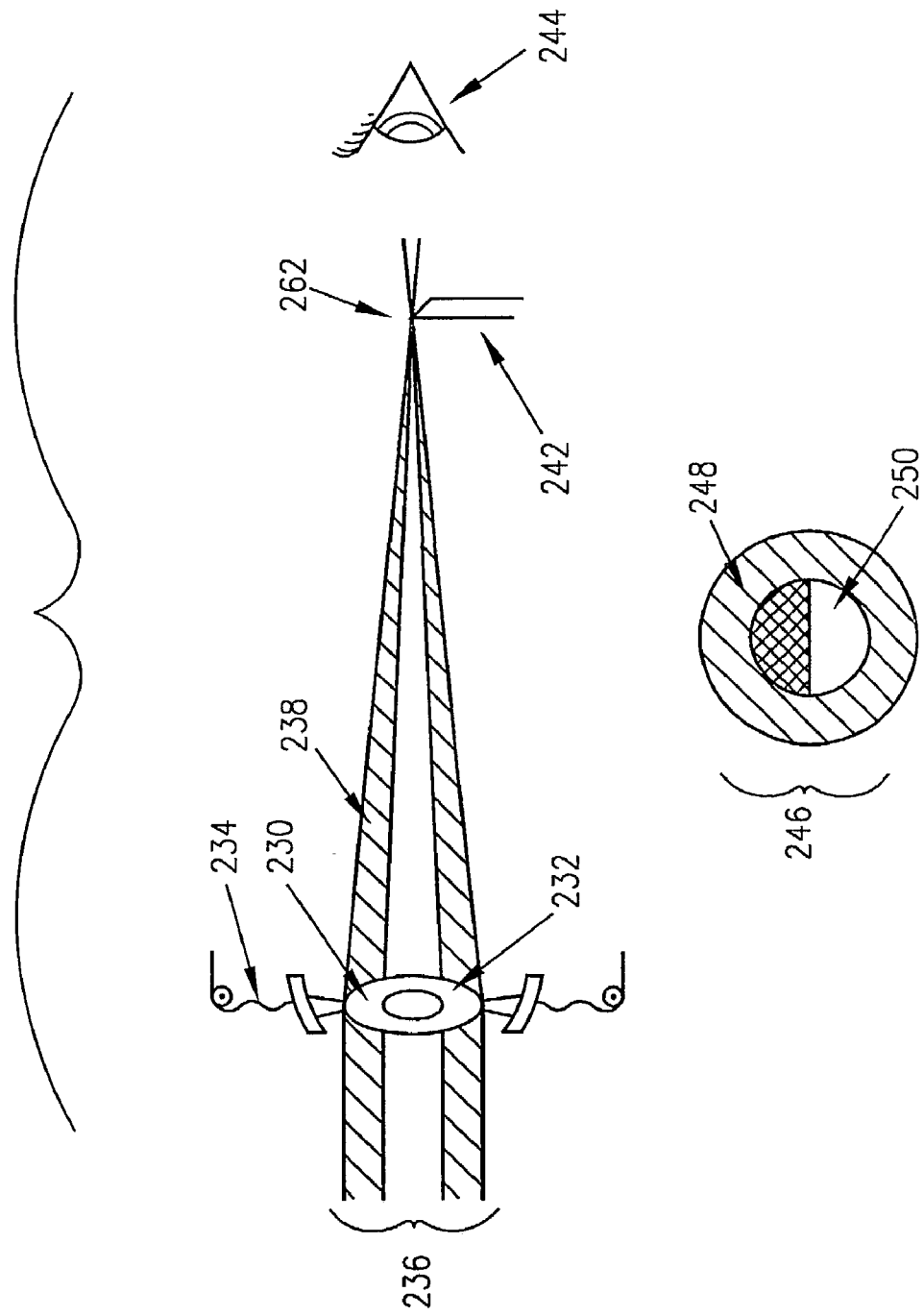

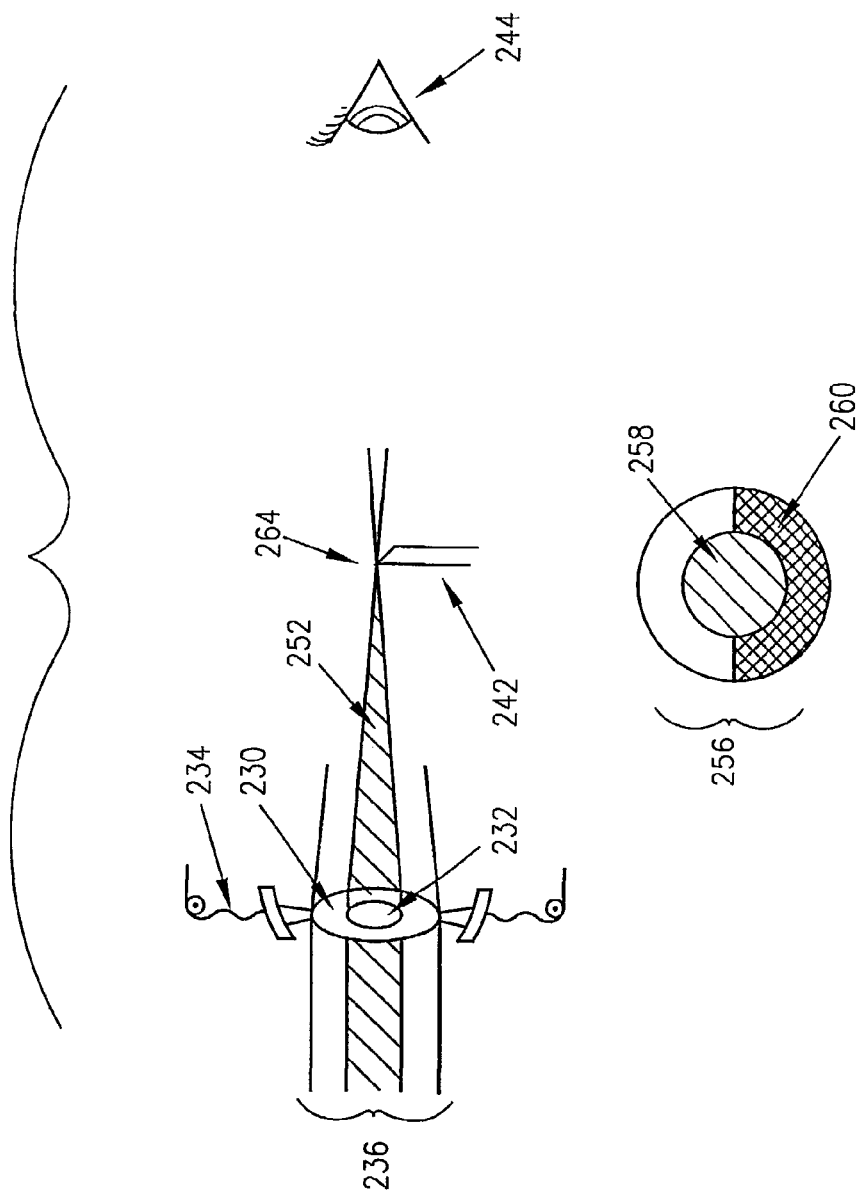

SUPPLEMENTARY ENDO-CAPSULAR LENS AND METHOD OF IMPLANTATION

This application is a 371 of PCT/US01/14728 filed May 8, 2001.

FIELD OF THE INVENTION

The present invention is directed to the field of surgical techniques and apparatuses designed to restore accommodation to eyes that have sustained lens removal.

BACKGROUND OF THE INVENTION

The human eye comprises a roughly spherical organ having essentially three distinct layers of tissue divided into three basic chambers. The tough outer sclerotic coat serves as a protective barrier for the eye, and forms the transparent cornea through which light passes into the eye. The sclerotic coat is composed of dense collagenous tissue. The middle choroid coat forms the iris, a diaphragm that controls the amount of light admitted into the interior of the eye through the pupil. The transparent crystalline lens is immediately posterior to the iris, and is held in place by zonular fibers attached to ciliary processes surrounding the crystalline lens. The zonular fibers collectively culminate in the suspensory ligament of the lens. The region between the cornea and crystalline lens is denoted the anterior chamber of the eye, whereas the gap created between portions of the crystalline lens and iris is known as the posterior chamber. Ciliary processes generate aqueous humor, which fills the anterior chamber and posterior chamber. Aqueous humor provides for nutrient and metabolic exchange between the avascular cornea, crystalline lens, and iris. The posterior pole of the crystalline lens abuts the hyaloid fossa of the posterior vitreous chamber of the eye.

Accommodation is the process of changing the focus of the eye between near and distant objects. Accommodation is achieved by constricting and relaxing the ciliary muscle connected to the crystalline lens via the zonular ligament. Such movement by the ciliary muscle serves to shape the crystalline lens to the appropriate optical configuration for focussing light rays from these objects onto the inner coat of the eye, structurally known as the retina.

The crystalline lens is a biconvex body, having an anterior convexity less steep and of a greater radius of curvature than its more parabolic posterior convexity. The lens is composed of elongated, prismatic cells known as lens fibers, which are tightly packed to form lamellar structures. Intracellular granular crystallins within the lens fibers confer transparent and refractive characteristics upon the lens. Lens fiber structure and composition varies within the lens, such that a firm central nucleus may be distinguished from a softer surrounding cortex. The entire lens is encompassed by the lens capsule (capsula lentis), a basement membrane into which the zonular fibers are inserted. The elastic lens capsule is composed of collagen fibers, glycosaminoglycans and glycoproteins. Due to its elastic properties, the lens capsule can stretch substantially in circumference without tearing.

A variety of disorders are known to impair or destroy normal function of the eye, including disorders of the lens, such as cataracts and presbyopia. Cataracts arise from progressive clouding of the crystalline lens, which, if left untreated, eventually scatters and obscures light rays from focussing on the retina. Historically, cataracts were surgically treated by either intracapsular removal of the entire lens structure, including the outer lens capsule and the inner crystalline lens matter, or extracapsular removal of the central portion of the anterior capsule and the crystalline lens matter, leaving in place the posterior lens capsule, the latter treatment of which is known in the art as the ECCE procedure. These procedures are prone to complications, such as retinal detachment, and, in the case of extracapsular cataract extraction, opacification of the posterior capsule.

As the crystalline lens ages, it becomes less flexible and gradually loses the ability to change shape in response to the contraction of the ciliary muscle. This is manifested in humans as a gradual loss of the ability to increase the refracting power of the lens and consequent reduction in the ability to focus the eye on nearer objects. This loss of focusing ability is called presbyopia.

Presbyopia is most commonly treated by bifocal and other multifocal spectacles and contact lenses. These devices typically comprise discrete zones of differing optical power through which the wearer's gaze is selectively directed to obtain a clear image for a given viewing distance. Common disadvantages are that these refracting powers are static and they are restricted to specific gaze positions. Other types of multifocal contact lenses and intraocular lenses are designed to simultaneously produce images through multiple refractive zones. A common disadvantage of these devices is that the contrast of the focused part of the image is reduced by the poorly focussed portions of the image.

Recently developed lens refilling procedures may reduce the incidence of many complications associated with traditional crystalline lens extraction and replacement treatment modalities. One such procedure is disclosed in U.S. Pat. No. 4,002,169, in which a rotary masticating tool is introduced into the lens structure via an inserted hollow needle. The capsular tissue contents, including the cataract, lens cortex and lens nucleus, are physically liquefied and then withdrawn from the lens capsule via suction through the needle. Such a process leaves the lens capsule intact as a capsular bag within the posterior chamber.

Often, a chemical treatment or sonication (phacoemulsification) is preferred over physical mastication for liquefying the lens. Following suction removal of the liquefied crystalline lens, the capsular bag may be flushed to remove remaining debris and then refilled with a molded synthetic lens. See, for example, the processes disclosed in U.S. Pat. No. 5,674,282.

Intraocular lenses may comprise relatively hard materials, relatively soft materials, or a combination of both types of materials. For example, methyl methacrylates, polysulfones or other relatively hard, biologically inert optical materials may be used alone, or in combination with softer biologically inert silicones, hydrogels or semi-rigid thermolabile materials. While these lenses restore optical transparency and, if comprising the appropriate optical power, can cause the eye to produce clear images of distant objects, their optical power is static and therefore can not change focal length as the viewing distances change.

Other intraocular lenses have multiple zones of varying curvature to provide a range of static refracting powers. These are generally referred to as bifocal or multifocal intraocular lenses. The retinal image produced by such lenses contains focussed and defocussed images. The defocussed images reduce the contrast of the focused image and therefore reduce the ability of the eye to obtain good resolution for all viewing distances.

A new lens may be created in situ in the lens capsule with a filler material having the appropriate characteristics to mimic the function of the natural crystalline lens. Many ophthalmic procedures designed to restore accommodation of the eye, such as lens refilling procedures for the correction of presbyopia and cataracts, rely on the replacement of endogenous lens matrix material with a transparent material of similar consistency and index of refraction and spectra.

Some of the preferred materials for filling the capsular bag comprise UV-curable polymers that require exposure to ultraviolet light to induce crosslinking. Such crosslinking typically requires creating two openings in the wall of the eye via bimanual surgery, which occupies both hands of the ophthalmic surgeon. Alternatively, crosslinking may be effected through the cornea, but such procedures may damage corneal tissues.

U.S. Pat. No. 5,391,590 discloses compositions useful as injectable intraocular lens material. Examples of polymerizable formulations include one or more polyorganosiloxanes having a vinyl functionality, a silicon-bonded hydride group, and the like. Such compositions may comprise soft, fast curing, low temperature vulcanization silicone gels capable of in situ polymerization, within the capsular bag. High molecular weight, high viscosity silicone precursor fluids are preferred, as they are less likely to leak from the injection site prior to polymerization. Such high viscosity materials only require a low cross-linking density to achieve an elastic modulus similar to a human crystalline lens. However, a reduced cross-linking density of these polymers results in an unacceptable gummy product having low resilience.

Certain low viscosity, low molecular weight fluids have desirable properties upon cure for injectable ocular lenses, but readily leak from the injection site. Upon curing of leaked gel, a bump may form on the surface of a refilled capsule. Such bumps are known to irritate the iris and mediate corneal edema. In an attempt to overcome this limitation, suitable low molecular weight fluids may be pre-cured to induce polymerization prior to injection into the lens capsular bag. Injection of such partially polymerized materials through a cannula may cause shear stress, which results in rough areas of the polymerized material that impair the function of the synthetic lens. Additionally, pre-cured polymer materials typically must be injected shortly after initiating crosslinking to prevent disadvantageous over-curing and reduced flow through the cannula.

Typically, the capsular bag tends to under fill unless very high density materials, such as gels having a viscosity of greater than $4 \times 10^6$ cS, are used. As mentioned hereinabove, viscous liquids and gels having less than $1 \times 10^6$ cS viscosity or soft gels are injected and introduced into the capsular bag, such fluids often leak from the bag. Leakage of such materials into the anterior chamber of the eye may cause a number of ocular problems, and endanger delicate ocular structures. For example, intraocular inflammation may be spurred by a foreign body reaction of the eye in response to the leaked material. Additionally, leaching of non-endogenous liquids or gels from the capsular bag may cause glaucoma, due to blockades of trabeculae and associated increases in intraocular pressure due to increased volumes of aqueous humor. Undesirable conditions, such as interference with motion of the iris and impairment of the optics of the eye due to glare are also known to occur upon escape of viscous liquids and gels introduced to the capsular bag.

Similarly, cataract surgery may require the introduction of a chemical agent to liquefy nuclear matter, and/or injection of a chemical or pharmacological agent to kill lens epithelial cells or impair their replication. Leakage of antimitotic compounds or hypoosmolar solutions destroys healthy, non-regenerative corneal endothelial and retinal cells of the eye, as opposed to the intended hyperproliferative lens epithelium.

An anterior capsulotomy, specifically a capsulorhexis, is typically used to reduce some of the procedural and post-operative complications associated with extracapsular and lens refilling protocols. A continuous tear capsulorhexis involves preparing a circular or round capsulotomy in the anterior lens capsule. In cases of ECCE, and peripherally in the case of lens refilling, and removing the essentially circular portion of the anterior capsule delineated by the continuous tear line, a continuous tear capsulorhexis forms an essentially circular tear line substantially coaxial with the lens axis.

Preferably, the capsulotomy is positioned within the zonule-free area of the anterior lens capsule. This type of capsulotomy forms a circular opening in the anterior lens capsule, through which cataractous lens matrix may be extracted by, for example, phacoemulsification and aspiration. What remains is a capsular bag having an elastic posterior capsule, an anterior capsular remnant about the anterior capsulotomy, and an annular capsular bag sulcus between the anterior capsule remnant and the outer circumference of the posterior capsule. Thus, the capsular bag remains attached to the surrounding ciliary muscle of the eye via the zonules, and is responsive to ciliary contraction and relaxation during accommodation.

Although continuous tear capsulorhexis is designed to provide an anterior capsule remnant or rim having a relatively smooth, continuous inner edge abutting the capsulotomy, the anterior rim is sometimes torn, radially sliced, or nicked during this procedure. Such damage to the anterior rim leaves the rim vulnerable to tearing radially when the rim is stressed, particularly upon insertion of instruments for manipulating the capsular lens matrix. Tearing of the lens capsule during capsulorhexis increases the likelihood of untoward leakage of materials injected into the evacuated capsular bag during lens refilling. To reduce the risk of such tearing, a deep anterior chamber is maintained throughout the surgery using a balanced salt solution or a viscoelastic material to fill the chamber. However, tears may arise despite taking such precautionary measures.

In an effort to address some of these ongoing problems in ophthalmic surgery, Nishi et al. (*Graefe's Arch Clin Exp Ophthamol* (1990) 228:582–588) developed a new disk for small-incision surgery, which also serves to seal the capsular opening. Following a circular mini-capsulorhexis and phacoemulsification procedures, an acrylamide synthetic disk larger than the capsular opening is inserted into the opening. After injecting a visco-elastic material into the capsular bag and anterior chamber of the eye, the disk is inserted into the anterior chamber. The disk is then manipulated such that the disk is choked by the entire capsular margin along its circumference, thereby fixing the disk in place of the missing portion of anterior capsule. Since the disk seals the opening of the lens capsule, the lens capsular bag is capable of refilling. Thus, a replacement material, polyacrylamide gel, is injected into the capsular bag to expand the bag. Although generally successful, certain drawbacks exist with this process, including expansion of the capsulorhexis opening during filling, causing intraoperative leakage. Moreover, Nishi et al. reported difficulties achieving a reproducible, centrally positioned circular capsulorhexis of an appropriate size for securely holding the inserted synthetic lens in the capsular bag. Furthermore, patients receiving such implantation developed capsular bag distention causing blurred vision.

Nishi, et al. (*Arch Ophthalmol* (1998) 116(10):1358–1361) recently devised a tube having a flange made to fit a surgically generated capsulorhexis opening in a patient's capsular bag. This tube is actually an implant since it is permanently bonded to the edges of the capsulorhexis with a silicone-based adhesive. Thereafter, a clear gel is injected through the tube via a 30 gauge stainless steel cannula. After filling the capsular bag, an adhesive within the tube seals the tube. The tube is then cut to remove excess length, although the remaining tube slightly protrudes from the bag into the anterior chamber of the eye. The protrusion of this implant may mechanically interfere with motion of the iris, impairing pupillary opening and closing. Contact of the inner surface of the iris causes drag, which may interfere with ocular accommodation. In addition, the protruding tube may scratch the corneal endothelium upon rubbing of the patient's eye containing the implant. Such implants are susceptible to biocompatibility problems, and may cause severe inflammatory reactions within the eye.

The methods described above attempt to significantly restore the accommodative capacity of the eye. However, such methods have not been completely successful. A lens system and surgical method or protocol for restoring accommodation to an eye would be particularly advantageous.

SUMMARY OF THE INVENTION

In one embodiment, the present invention is directed to a method of simultaneously supplementing refractive power of an eye and increasing accommodative capacity of an eye. A phaco-ersatz procedure is performed on an eye to remove a lens from the lens capsule of an eye. A liquid is then introduced into the lens capsule, followed by inserting a supplemental endo-capsular lens (SECL) into the lens capsule. The SECL is positioned as desired in the lens capsule and the liquid is then cured.

In a further embodiment, the present invention is directed to a method of simultaneously supplementing refractive power of an eye and increasing accommodative capacity of an eye by performing a phaco-ersatz procedure to remove a lens from the lens capsule of an eye and introducing a fluid into the lens capsule, preferably through a capsulorhexis. The fluid is preferably a polymer, and more preferably is a polymer gel made from a material selected from the group consisting of siloxanes, hydrogels and combinations thereof. A SECL is then inserted into the lens capsule, preferably through the capsulorhexis, and positioned as desired in the gel in the lens capsule. The SECL is preferably made from a material selected from the group consisting of polydimethylsiloxane, hydroxyethyl methacrylate, methyl methacrylate, ethyl methacrylate, phenylethylacrylate, phenylethylmethylacrylate and combinations thereof. After positioning the SECL, the polymer preferably is cured. In alternate embodiments of the present invention, the SECL is first introduced into the lens capsule, followed by introducing the fluid. In a still further embodiment the SECL and the fluid are introduced into the lens capsule substantially simultaneously.

In a still further embodiment, the present invention is directed to a device for simultaneously supplementing refractive power of an eye and increasing accommodative capacity of an eye, the device comprising an amount of fluid inserted into an empty lens capsule of an eye, preferably through a capsulorhexis. The fluid is preferably a polymer, and more preferably is a polymer gel selected from the group consisting of siloxanes, hydrogels and combinations thereof. A SECL introduced into the lens capsule, preferably through the capsulorhexis, and positioned in situ in the fluid to achieve the desired refractive power and accommodative capacity. The fluid is then preferably cured.

In yet another embodiment, the present invention is directed to a device for simultaneously supplementing refractive power of an eye and increasing accommodative capacity of an eye comprising a fluid and a SECL inserted into an evacuated lens capsule. The fluid preferably is a polymer, and more preferably is a polymer gel preferably made from a material selected from the group consisting of siloxanes, hydrogels and combinations thereof. The SECL inserted into the lens capsule is positioned within the polymer gel with the SECL preferably made from a foldable material selected from the group consisting of polymethylphenylsiloxane, polyfluoropropylmethylsiloxane, hydroxyethyl methacrylate, methyl methacrylate, ethyl methacrylate, phenylethyl acrylate, phenylethylmethacrylate and combinations thereof.

BRIEF DESCRIPTION OF THE DRAWINGS

FIG. 3a shows an eye without the SECL for comparison, and FIG. 3b shows an eye with the SECL in place.

FIGS. 5a–5d are cross-sectional views of an eye showing the magnification characteristics that can be built into the SECL of the present invention.

FIGS. 11–14 are representative drawings of a lens-stretching measurement system for an ersatz lens having an SECL.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The present invention is directed to the incorporation of a supplementary endo-capsular lens (SECL) inserted or embedded within either a fluid, inside the capsule of the crystalline lens, during phaco-ersatz or similar surgical procedures to supplement the refractive power of the eye with a view to (1) correcting ametropia, while also (2) maintaining a useable amplitude of accommodation. The fluid preferably is a polymerizable polymer. More preferably, the polymer is in the state of a gel. The term gel is understood to encompass emulsions, suspensions, etc. Most preferably, the polymer gel is polymerizable and is a siloxane or hydrogel-containing polymer, or combination thereof. A hydrogel is understood to be any hydrated, crosslinked polymeric system that's contains water in an equilibrium state. Siloxanes are polymeric compounds comprising a polymeric backbone with relatively short poly(organosiloxane) side chains on the backbone polymer. The most suitable polymer gels for the present invention are those which can be crosslinked and therefore "cured" quickly (within from about 1–15 minutes) using UV light. However, it is understood that the present invention is not restricted to the used of curable polymers. In fact the present invention also contemplates the use of fluids which are not cured to be effective, such as sol-gels, or other thermo-reversible systems, etc. The fluids of the present invention to be introduced into the lens capsule preferably have a specific gravity of from about 0.90 to about 1.5, and more preferably from about 0.095 to about 1.45.

The SECL is primarily intended for use with phaco-ersatz or similar surgical procedures for the restoration of accommodation. However, use in other related surgical or refractive correction applications is also possible (e.g. vascular, heart or other organ, etc. applications). The SECL is preferably made from a material selected from the group consisting of polymethylphenylsiloxane, polyfluoropropylmethylsiloxane, hydroxyethyl methacrylate, methyl methacrylate, ethyl methacrylate, phenylethylacrylate, phenylethylmethylacrylate and combinations thereof.

Figure 1A:
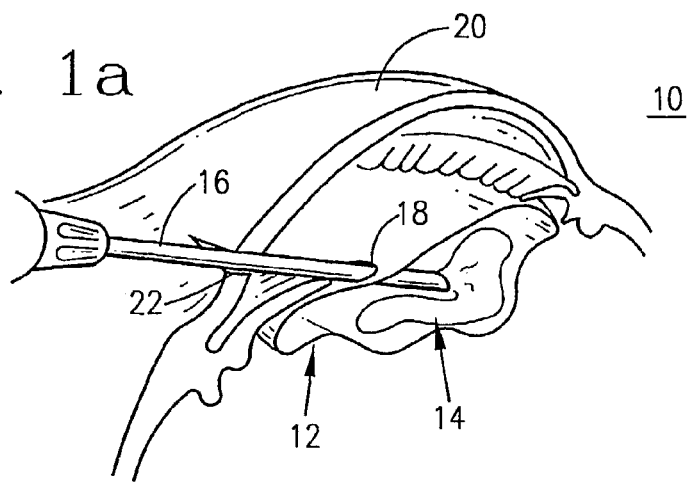
FIGS. 1a–1c are partial cut-away views showing one preferred embodiment of the present invention wherein a polymer gel is introduced into the lens capsule via a cannula (1a), followed by SECL insertion (1b) and placement (1c).

The operation, utility and applicability of the SECL can be understood from the following description of the preferred embodiments. In FIG. 1a, the crystalline lens of a myopic presbyope has been treated with the phaco-ersatz procedure. The lens (not shown) of eye 10 has already been removed from the lens capsule 12. A visco-elastic polymer gel 14 has been injected into the capsule 12 through the cannula 16 that has been inserted through a capsulorhexis 18 in the capsule 12 and a corneal incision 22 in the corneal wall 20 as part of the phaco-ersatz procedure.

Figure 1B:
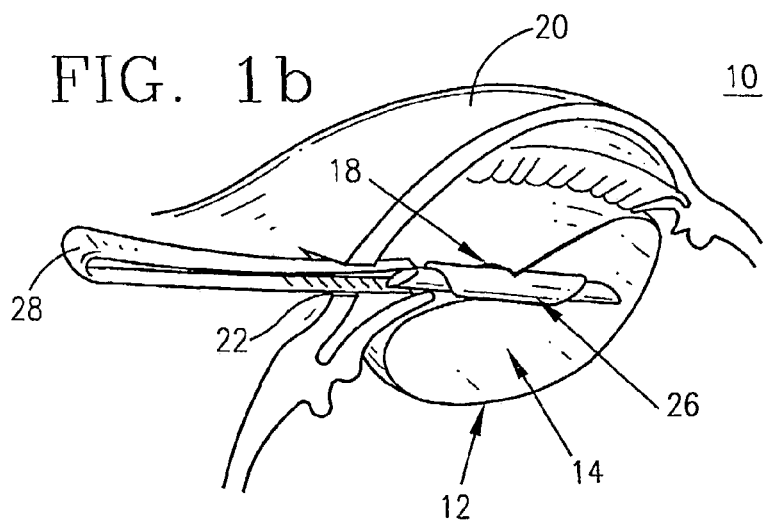
Figure 1C:
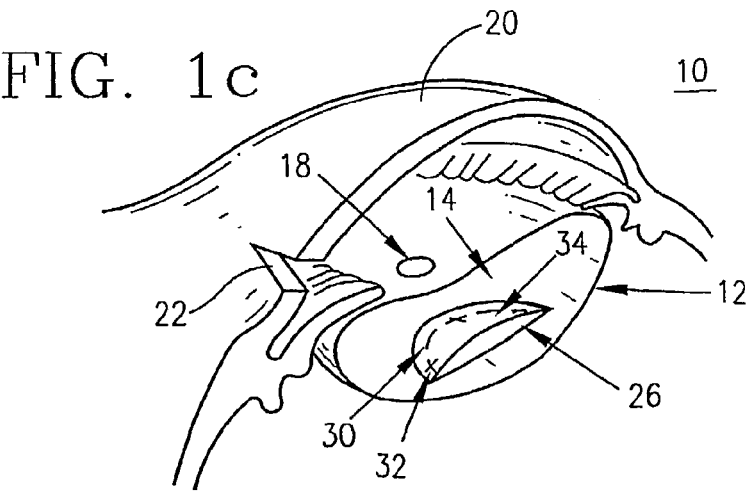

As shown in FIG. 1b, an SECL 26 in a compacted position, such as being folded or rolled, and preferably is introduced through capsulorhexis 18 and corneal incision 22 into the capsule 12. The SECL 26 is held and maneuvered with a lens holder 28. FIG. 1c shows the SECL 26 in a partially opened position within the capsule 12 suspended in the polymer gel 14. Positioning indicia 30, 32 are shown on the front surface 34 of the SECL 26.

Figure 2:
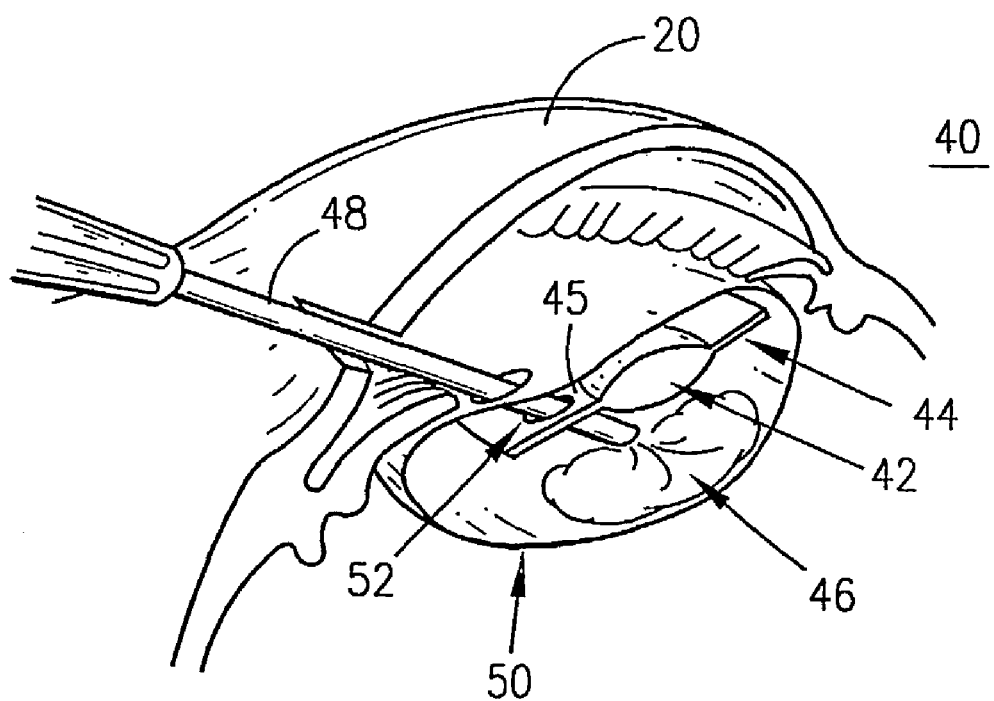
FIG. 2 is a partial cut-away view showing another embodiment of the invention wherein the SECL comprises a haptic to assist in orientation.

The SECL may also be designed to act as a valve that operates to provide gel retention functionality, thereby facilitating the injection of the phaco-ersatz polymer gel. FIG. 2 illustrates an alternate embodiment of the present invention wherein an eye 40 had had an SECL 42 implanted. The SECL 42 has haptic portions 44, 45 that assists in the centration and alignment of the SECL 42. As shown, the SECL 42 is implanted anteriorly within the capsule 50. As shown, to facilitate injection of the polymer gel 46 through the cannula 48 into the capsule 50 (as part of the phaco-ersatz procedure), an access opening 52 is provided at haptic portion 45.

Figure 3A:
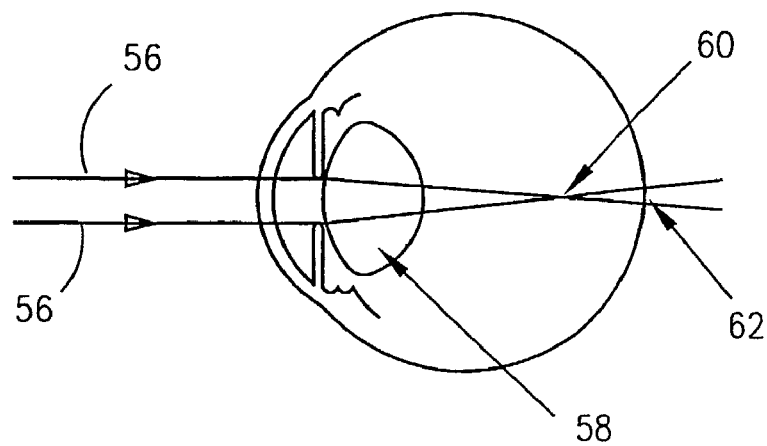
FIGS. 3a and 3b show the benefits of the SECL placement in cross-sectional views of an eye.
Figure 3B:
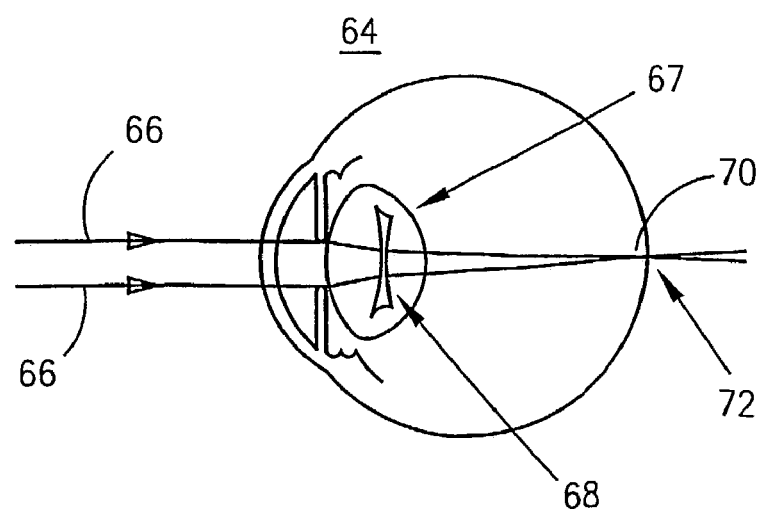

FIGS. 3a and 3b illustrate the advantage of the SECL of the present invention when used in combination with a phaco-ersatz or similar surgical procedure for correcting combined ametropia and presbyopia. In FIG. 3a, a standard phaco-ersatz procedure is performed without a SECL. In this embodiment, the myopic eye 54, while having accommodation restored, will retain its original myopic state. Thus, light rays 56 from a viewing object (not shown) located at a long distance from the eye to the left, will be focused by the lens 58, which has undergone phaco-ersatz, to a focus 60 in front of the retina 62. Consequently, the retinal image of the distant object will be blurred.

In FIG. 3b, by using the SECL following the same surgery, due to the additional refraction afforded by the SECL of the present invention in a myopic eye 64, simultaneous correction of ametropia is achieved with restoration of accommodation. In this situation, light rays 66 from a distant viewing object (not shown) will now be focused by the ersatz lens 67, which has had a SECL 68 inserted. Due to the additional and correct power afforded by the SECL 68, the light rays are now focused onto the retina 72. The outcome is a clear and sharp retinal image 70 of the object.

FIG. 4 illustrates advantages of the SECL. As shown in FIGS. 4a and 4b, a conventional ametropia correction is provided following a phaco-ersatz operation. Due to the documented change in aberration state of an eye when it focuses to "near" for reading, aberration of the eye cannot be corrected through the entire range of vision (from distance to near).

Figure 4A:
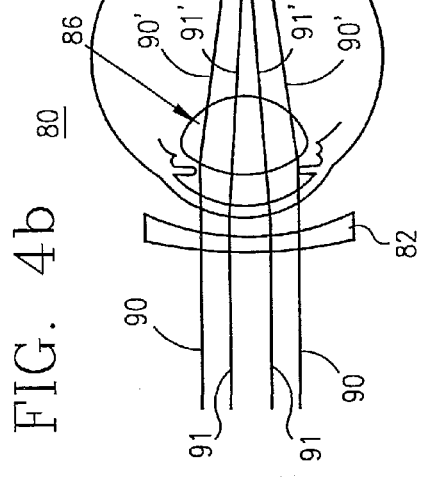
FIGS. 4a–4d are cross-sectional views of an eye showing the aberration control characteristics that can be built into the SECL of the present invention.

In FIG. 4a, an eye 80 which has undergone the phaco-ersatz procedure for restoring accommodation and wearing a spectacle lens correction 82 for ametropia, has its accommodation relaxed for viewing a distant object. In this situation, light rays 84, 85 from the distant viewing object are focused by the eye with relaxed ersatz lens 86 towards the retina 88. However, due to the presence of ocular aberrations, the more peripheral light rays 85' are focused further in front 87 of the retina 88 than the more axial light rays 84'. This difference in focus 89 of peripheral rays 85' and axial rays 84' produces spherical aberration which degrades the retinal image quality.

Figure 4B:
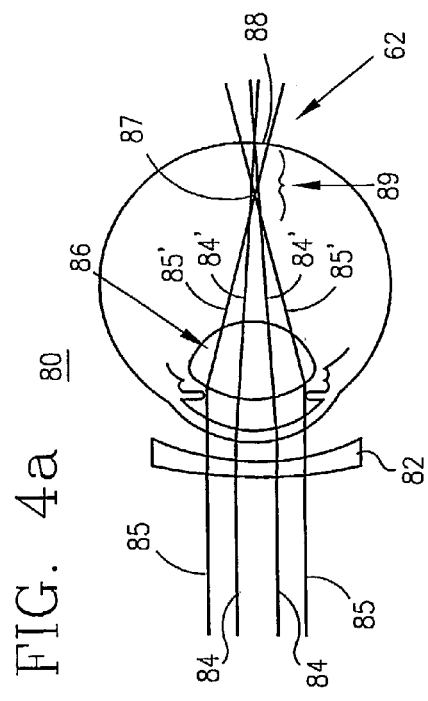

In FIG. 4b, the same eye 80 with the same spectacle correction 82 is now focused for near viewing. The light rays 90, 91 from the near viewing object, are focused by the eye with accommodated ersatz lens 86 towards the retina 88. Due to a change in the aberration of the eye at near focus, the peripheral rays 90' are now focused further behind 92 the retina 88 than the axial rays 91'. Due to this change in aberration on accommodation, the fixed focused spectacle 82 is not able to provide an optimum focus at both distant and near viewing.

Figure 4C:
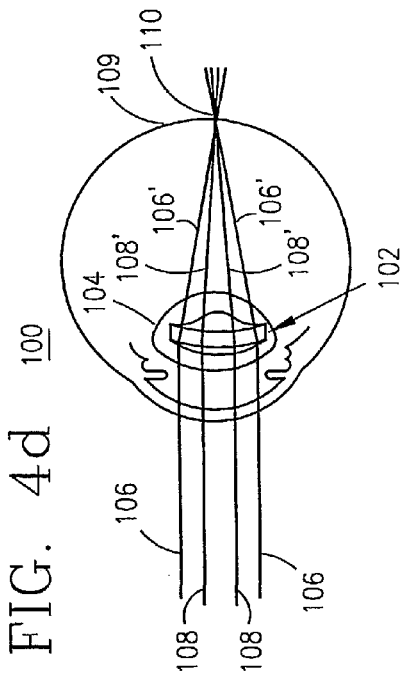
Figure 4D:
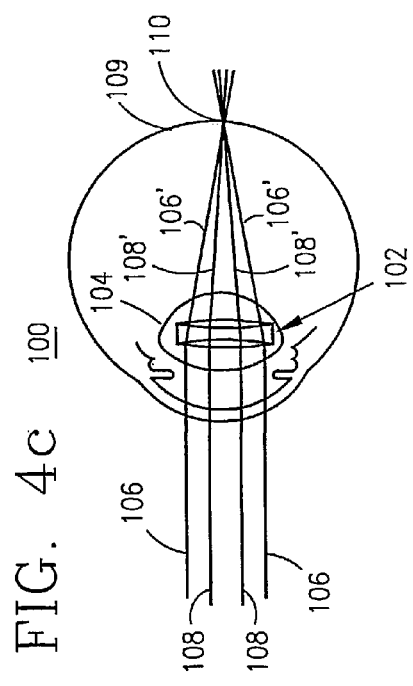

In FIGS. 4c and 4d, a SECL is shown that is specifically designed and inserted to control the aberration at both distance and near vision. In FIGS. 4c and 4d, an eye 100 has a SECL 102 implanted into the lens 104 along with the phaco-ersatz procedure. The SECL 102 has a mechanical flexibility designed so that the SECL 102 will bend in a controlled manner when the ersatz lens 104 accommodates. In FIG. 4c, during relaxed accommodation, light rays 106, 108 from a distance viewing object are focused by the eye 100 with the ersatz lens 104 and the SECL 102 towards the retina 109. Since the profile of the SECL 102 has been designed to reduce aberrations, both peripheral rays 106' and axial rays 108' are now focused to a single focus 110 on the retina 109.

In FIG. 4d, with the accommodation exerted for near viewing, light rays 106, 108 from a near object are focused by the eye 100 with the ersatz lens 104 and the SECL 102 towards the retina 109. Given the appropriate and controlled bending of the lens on accommodation, the lens form of the SECL 102 will change, thereby altering its aberration characteristics. In this way, both peripheral rays 106' and axial rays 108' are still focused to a single focus 110 on the retina 109. The implementation of the SECL 102 therefore provides significantly improved visual performance at both distance and near vision.

In addition, magnification may be built into the optics of the SECL. By designing into the optical system of the SECL characteristics such as telescopic optics or controlled field distortions, the SECL may be used to not only correct for ametropia and aberrations, but also to facilitate and enhance vision in conditions of amblyopia or visual field defects (e.g. scotoma). FIGS. 5a and 5b show advantages of the present invention whereby, as shown, a SECL with reduced magnification is used to increase the patient's effective field of view.

In FIG. 5a, an eye 120 which has undergone phaco-ersatz will retain its original magnification and field of view. Thus, objects spread across the field of view such as the three letter "F"s 122 will be focussed 124 to a certain area 125 across the retina 126. In FIG. 5b, an eye 130 has undergone phaco-ersatz with an addition of a magnification reducing SECL 132. In this embodiment, objects across the field of view 122 will be focussed to an area 131 on the retina 126 smaller than the corresponding retinal area of a non-SECL eye 120.

FIG. 5c shows an increased magnification SECL for assisting a patient with amblyopia. In this embodiment, the eye 140 has an ersatz-lens 141 having a magnifying SECL 142 such that objects across the field of view 122 will be focussed to a large area 144 across the retina 126.

FIG. 5d provides an example of an eye 150 in which barrel distortion is designed into a SECL 152 for providing increased central magnification yet with no loss in field of view in the periphery. Barrel distortion refers to the scenario whereby the magnification of an object decreases as it is placed further away from the line of sight. In this embodiment, the SECL 152 will magnify an object in the direction of viewing, such as the central letter "F" 154, while simultaneously reducing objects away from the direction of viewing, such as the two side letter "F"s 156, 157. Thus, the respective retinal images of these objects are simultaneously magnified 154' and reduced 156' and 157'.

Figure 6:
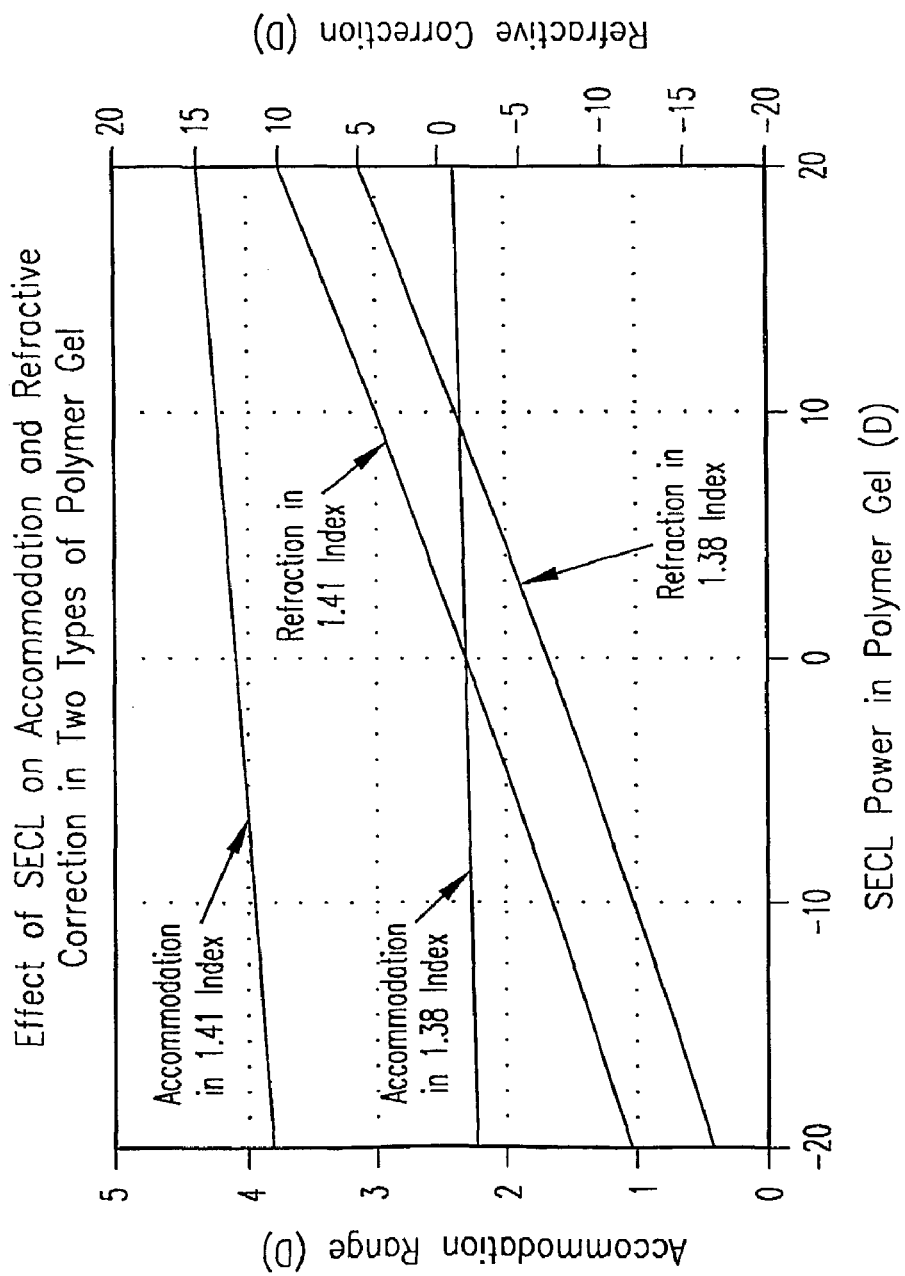
FIG. 6 is a chart showing the effect of the SECL of the present invention on both accommodation and correction of ametropia, also termed refractive correction.

FIG. 6 depicts a graph showing the refractive power needed in a SECL for correcting a range of ametropia. The horizontal axis of FIG. 6 represents increasing power (measured in diopters) of a SECL when measured immersed in the polymer gel used for phaco-ersatz. The left vertical axis refers to the amplitude of accommodation (also in diopters) which is derived by using a SECL of the corresponding power. The right vertical axis indicates the amount of ametropia (in diopters) which can be corrected by using the respective SECL power. For example, if phaco-ersatz is carried out using polymer gel with a refractive index of 1.41, then by the introduction of the SECL with −10 D of refractive power, then −7 D of myopia may be corrected with an accompanying amplitude of accommodation of just under 4 D. It should be kept in mind that depending on the design of the SECL (e.g. form factor, refractive index, thickness, location, etc), the relationship shown may vary. For example, the lens form or optical system design of the SECL may be designed to be able to compensate fully or partially for errors or variations in the refractive index of the gel or polymer. Similarly, the lens form or optical system design of the SECL may be altered to control aberrations, magnification or distortions to enhance vision.

The SECL may be placed in any position within the crystalline lens. The position (antero/posterior) of the SECL is chosen to control the relative contribution of the SECL to accommodative range, ametropia correction, and aberration and magnification control. Therefore it is understood that the present invention incorporates significant system flexibility such that the SECL characteristics in combination with the polymeric gel characteristics can be selected to meet the patient's needs.

Figure 7:
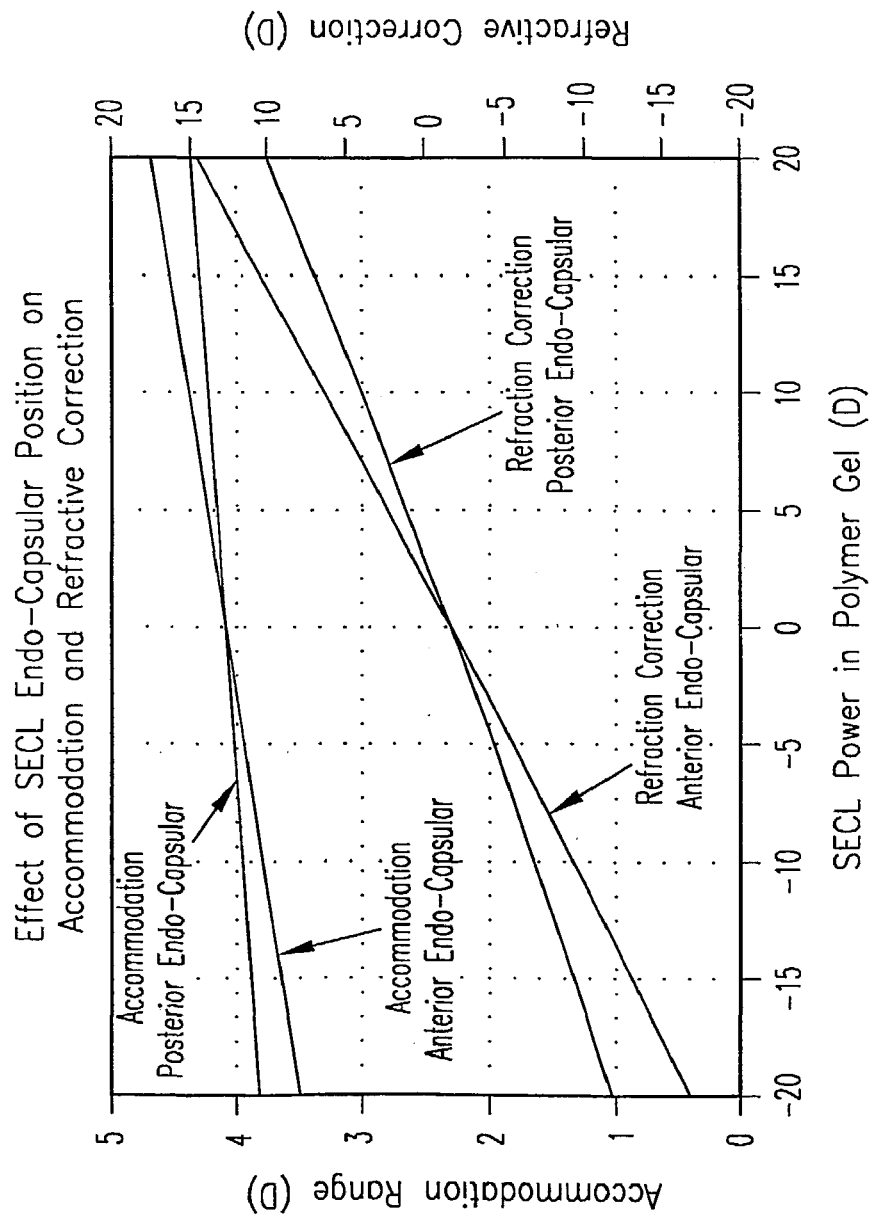
FIG. 7 is a chart showing the effect of the SECL endocapsular position on both accommodation and refractive correction.

For example, the specific gravity of the material used in the SECL may be chosen to be optionally, higher, lower or equal to that of the introduced (preferably injected) polymer gel. This facilitates the antero-posterior positioning of the SECL. For example, FIG. 7 shows the behavior of the SECL with different refractive powers when placed anteriorly and posteriorly, illustrating the ability to control its contribution to accommodation and ametropia through its location. In FIG. 7, the horizontal axis represents increasing power (measured in diopters) of a SECL when measured immersed in the polymer gel used for phaco-ersatz. The left vertical axis refers to the amplitude of accommodation (also in diopters) which is derived by using a SECL of the corresponding power. The right vertical axis indicates the amount of ametropia (in diopters) which can be corrected by using the respective SECL power. The plotted curves indicate the correction and amplitude of accommodation. For example, when a SECL of −15 D is placed at the anterior of (and inside) the ersatz lens, it will correct −13 D of myopia while providing about 3.7 D of accommodation. The same SECL when placed posteriorly inside the ersatz lens will correct −9 D of myopia while returning almost 4 D of accommodation.

In addition, it is understood that the SECL is preferably designed to facilitate it being compacted by being rolled upon itself into a cylindrical configuration to allow it to be passed through a capsulorhexis, preferably having a diameter of less than about 1 mm. The SECL could also be folded or otherwise compacted such that it can be passed through the capsulorhexis and then expanded into its desired, final "open" configuration in the lens capsule, suspended in the injected fluid.

Special targets or alignment features may be placed on the surface of, or embedded into the substance of the SECL to facilitate optical centration and lateral positioning/alignment of the SECL. In addition, features for facilitating the alignment and positioning of the SECL may be incorporated. For example, two, three or more thin haptics (or a thin haptic skirt) may be provided on the SECL for this purpose.

Figure 8:
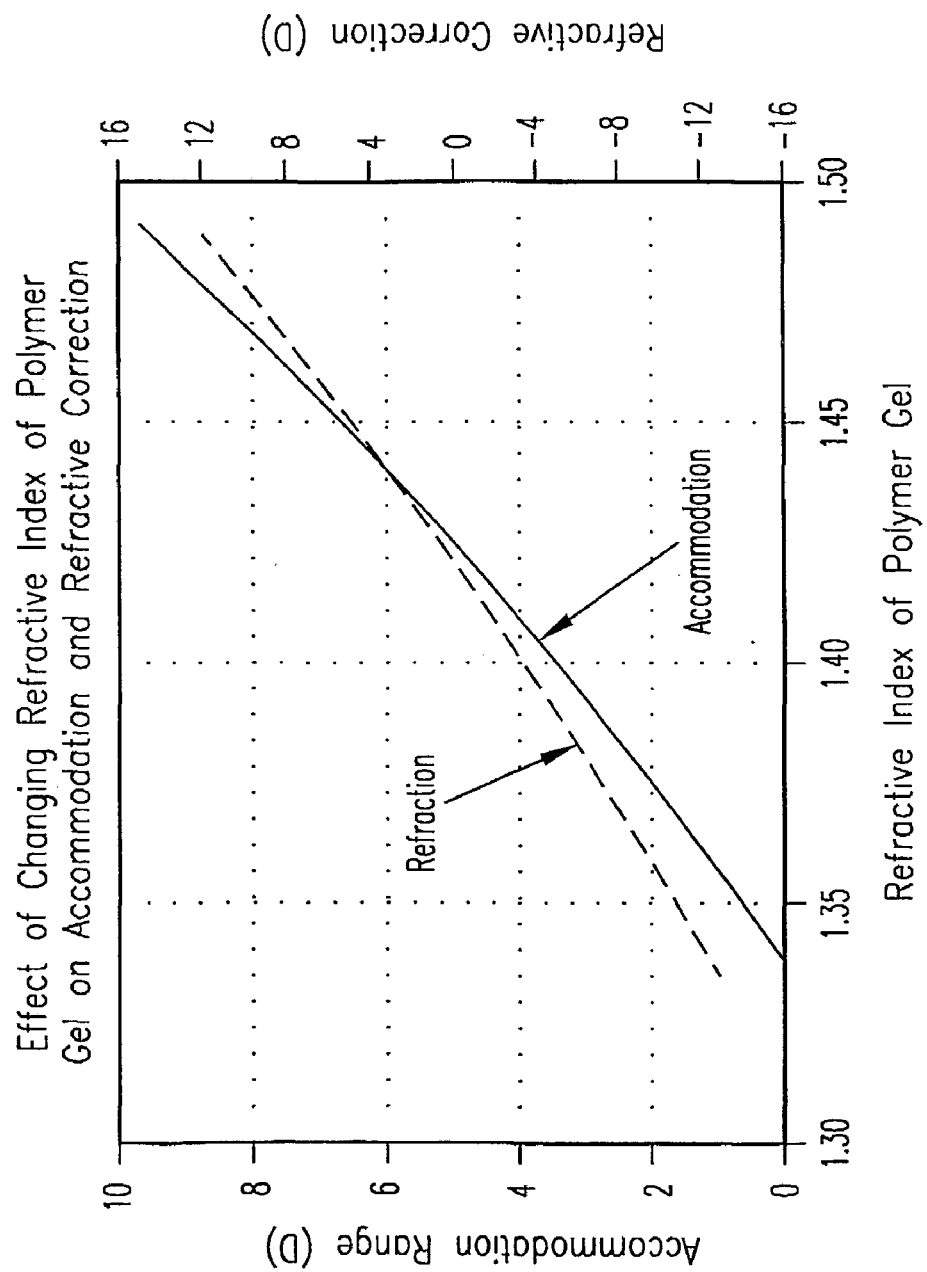
FIG. 8 is a graph showing the effect of changing refractive index of the polymer gel on both accommodation and refractive correction.
Figure 9:
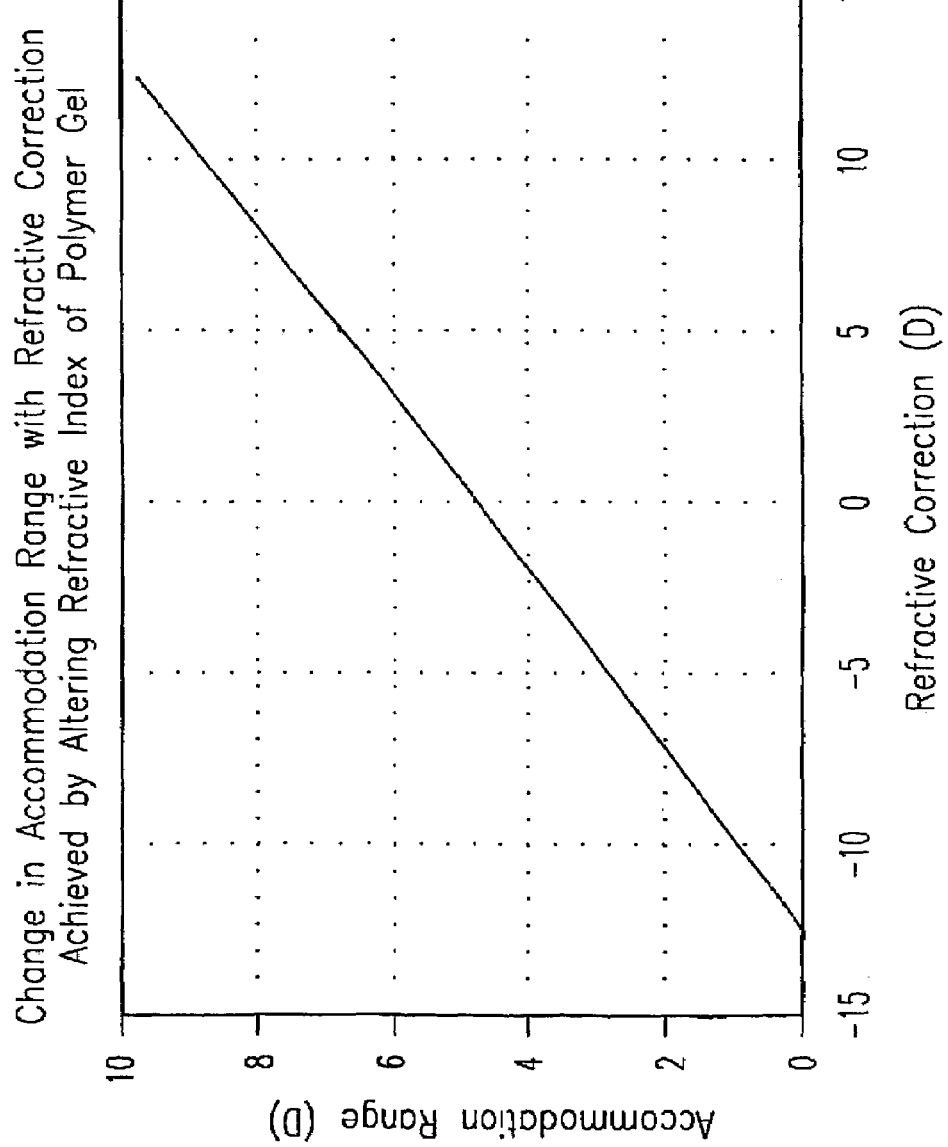
FIG. 9 is a graph showing the change in accommodation range with refractive correction achieved by altering the refractive index of the polymer gel.

FIG. 9 is a chart demonstrating the amount of accommodative range available to the eye when ametropia correction is attempted by altering refractive index. In can be noted that, when a myopia correction of −10 D is attempted by altering refractive index, the post-surgical eye only has 1 D of resultant accommodation—almost as poor as the original presbyopic eye. Thus, the availability of a range of refractive index in a polymer gel (which may not be feasible from a polymer chemistry standpoint) is necessary. Further, the ametropia correction accuracy is critically dependent on the accuracy to which the refractive index of the polymer gel may be fabricated. Note from the slope of the line in FIG. 8 that a 0.01 error in polymer refractive index translates to a 1.67 D error in ametropia correction. This level of accuracy may not be achievable in a physiological environment.

It is known that with over or under-filling of the capsule, while the refractive power of the lens may be altered to correct ametropia, the accommodative range is also affected. Over-filling, which is used to correct myopia, also reduces the range of accommodation available. Due to the tensile strength of the capsule, there is a limit to the extent to which the capsule may be over-filled. Hence, there is a limit to the range of myopia which can be corrected. Further, a minimum volume of polymer gel is required to maintain a smoothly injected capsule without ripples or warpage. Under-filling below this volume severely degrades vision. Thus, there is also a limit to the range of hypermetropia that can be corrected. With over and under-filling, the accommodative range made available is inextricably linked to the magnitude of ametropia correction targeted. Therefore, the present invention, for the first time corrects ametropia within the phaco-ersatz procedure, but does not adversely impact the accommodative range affordable to the post-surgical eye.

With the phaco-ersatz or similar procedures, the reliance on the refractive index of the gel or polymer to correct ametropia introduces some limitations. First, the range of ametropia that can be corrected is limited by the availability of a range of gel refractive index. Second, the accuracy to which ametropia may be corrected is critically dependent on the accuracy to which gel refractive index can be fabricated. An error of 0.01 in a gel of refractive index 1.39 can cause an error in refractive correction of approximately 1.7 D (See FIG. 8). Third, there is a reciprocal relationship between the amount of ametropia correctable and the range of accommodation afforded (See FIG. 9). This means that myopes, especially medium to high myopes, will have a resultant insufficient range of accommodation.

The SECL of the present invention will supplement the refractive power of the phaco-ersatz lens (and hence eye) thereby enabling the eye to be corrected for ametropia simultaneously, and without compromising the accommodative range of the eye (as may occur if ametropia is corrected solely by varying the refractive index of the polymer gel). Therefore, the SECL of the present invention can partially or totally correct astigmatic refractive errors by selecting a material for the SECL having the appropriate refractive index and lens form, or optical system design, along different meridians, and by controlling the SECL's orientation within the capsule. Similarly, the present SECL, by the appropriate choice of refractive index and lens form or optical system design, can partially or totally compensate for errors or variations in the refractive index of the gel or polymer. In addition, by selecting an appropriate refractive index and lens form or optical system design, the SECL of the present invention can partially or totally control the aberration of the eye at near and distance viewing, or provide suitable magnification or controlled distortion to improve vision for a range of visual defects (e.g. amblyopia, visual field defects).

According to one preferred embodiment of the present invention, the SECL of the present invention has a lower refractive index than the polymer gel. As shown in FIG. 1, the SECL shown therein is a convex lens form. Given the convex lens form, such a SECL will have a negative refractive power when located inside the polymer gel that has a comparatively higher refractive index. The surface profiles and thickness of such SECLs are calculated (keeping in mind the refractive indices of the SECL and the injected polymer gel, and the final positioning of the SECL) such that its effective power at the spectacle plane is equal to the patient's state of myopia. Given a particular patient's myopic state, and the desire to maximize the range of accommodation of the patient, the SECL is positioned adjacent to the posterior capsular surface (FIG. 1c, and FIG. 7 for explanation).

The implementation process of the SECL of the present invention is facilitated by three additional features of the SECL. First, the mechanical properties of the SECL including its elastic modulus, tensile strength and pliability were selected to allow compacting the SECL, such as by rolling or folding the SECL during implantation (See FIG. 1b). This permits the SECL to be introduced into the capsular bag via the same capsulorhexis made during the phaco-ersatz procedure without widening the existing capsulorhexis, or needing to create another capsulorhexis. Second, anteroposterior positioning of the SECL during implantation was facilitated by choosing a material having a higher specific gravity than the polymer gel. During implantation, when the patient is in the supine position, the SECL would drop into the posterior position without additionally complicating manipulation on the part of the surgeon (See FIG. 1c). To further assist lens positioning during implementation, the SECL preferably has a series of alignment targets and marks integrated into the SECL. These features are visible through the high power surgical microscope and assist the surgeon in achieving the ideal lateral alignment and optical centration of the SECL (See FIG. 1c). These alignment features, or targets, may be embossed, molded, etched or laser scribed onto the surface of, or embedded into the substance of the SECL to facilitate optical centration and lateral positioning/alignment of the SECL. Since these features may be made very small, and lies near the exit pupil of the patient's eye, it will not affect visual performance.

As shown in FIG. 1b, the SECL is introduced to the lens capsule preferably through the use of a cannula having the appropriate diameter, (preferably less than about 1 mm). The cannula should appropriately grip the SECL in the compact (rolled) state and assist in inserting the SECL through the capsulorhexis. The cannula should then appropriately release the SECL in the desired location within the lens capsule, into the polymer gel.

Figure 10:
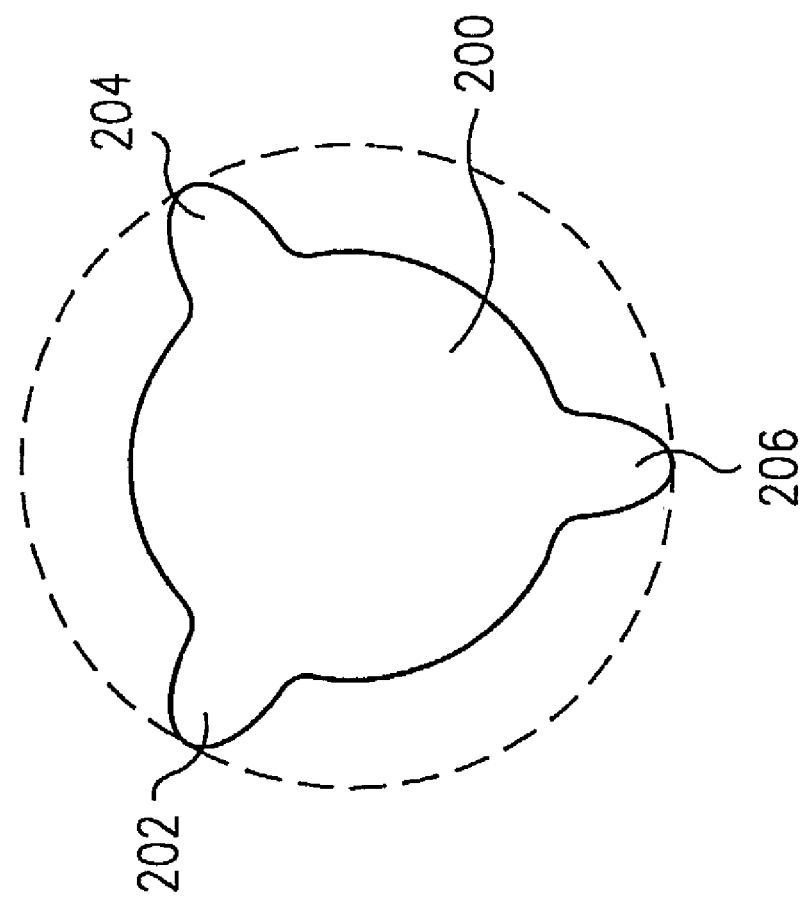
FIG. 10 is a plan view of a SECL having a tri-haptic configuration.

Still further, other devices or features for facilitating the alignment and positioning of the SECL may be incorporated. For example, one or more thin haptics may be provided on the SECL for this purpose. Another example is the use of a thin haptic skirt that may be equal or slightly smaller in diameter than the equatorial diameter of the crystalline lens in its accommodated state. FIG. 10 shows a SECL 200 in the unfolded position having three haptics 202, 204, 206. This embodiment is thought to facilitate optimum positioning while exerting equal force outwardly on the lens. It is understood that SECLs can be used having differing numbers of haptic "legs", and that the "legs" may be any useful shape or configuration.

Although not an essential requirement, the SECL may be designed, either by manipulating its geometry, or by its material properties, to flex during accommodation.

The SECL may consist of a simple singlet lens, a compound lens, a lens train or system, or non-conventional optical systems including but not limited to Fresnel, diffractive or holographic optics, gradient refractive index (GRIN) system, or any combinations of these. Further, while a conventional design may make use of materials which are higher than the surrounding media for the SECL, one particularly useful variation of the SECL is to use materials of a lower refractive index than that of the surrounding media, or a combination of components with higher and lower refractive indices. In addition, by using the appropriate optical design for a SECL, variations in the refractive index of the phaco-ersatz gel may be compensated for, such that their impact on the resultant ametropia and accommodative range may be minimized or eliminated.

The refractive power of the SECL is selected to provide the appropriate amount of refractive power to correct the ametropic eye. The refractive power of the SECL is chosen so that in situ, its overall effect on the refractive power of the eye is equal and opposite to the ametropia of the eye. Thus in this description of the invention, the refractive power of the SECL always refers to its refractive power when surrounded by the fluid that is introduced, preferably injected, into the lens capsule. In this way, the SECL can correct ametropia while allowing the primary procedure (e.g. phaco-ersatz) to produce the accommodative range. The ametropia correctable may be spherical or cylindrical power or a combination of both. Prismatic power may also be incorporated in special cases.

The specific gravity (relative weight) of the material used for fabricating the SECL may be chosen to be optionally, higher, lower or equal to that of the injected polymer gel. The availability of this option assists in the antero-posterior positioning of the SECL. Preferably, the specific gravity of the SECL is from about 0.9 to about 1.5, and more preferably is from about 0.95 to about 1.45.

Preferably, the effective refractive power of the SECL is chosen so that, in situ, its overall effect on the refractive power of the eye is equal and opposite to the residual ametropia of the eye having undergone the phaco-ersatz procedure. Thus in this description of the invention, the ametropia of the eye always refers to its post phaco-ersatz refractive error without the SECL. In this way, the SECL can correct ametropia while allowing the primary procedure (e.g. phaco-ersatz) to provide the accommodative range. The ametropia correctable may be spherical or cylindrical in power, or a combination of both. For special cases, prismatic power can be incorporated. Therefore, one advantage of using a SECL in combination with the phaco-ersatz or similar surgical procedures is the simultaneous correction of ametropia without significantly impairing the range of accommodation restored by the surgical procedure.

Additionally, aberration control may be built into the optics of the SECL. The optical performance characteristics of the SECL may be designed to eliminate, compensate, control or enhance the aberration of the eye. Since the SECL is endo-capsular, the aberration characteristics may be designed to change with accommodation. For example, it is known that a shift in the spherical aberrations of the eye occurs when it focuses from distance to near which is not correctable by conventional means. Due to its endo-capsular nature, the SECL may be designed to eliminate, compensate, or control the aberration through the range of focus. The SECL may be placed in any position (antero-posteriorly or laterally) within the capsule in order to tune its characteristics, behavior and performance.

The polymeric gel as well as the SECL may comprise additives to enhance their optical performance. For example, any of a variety of tints may be used with the SECL and/or the gel. In addition to alignment marks and targets mentioned above, the SECL may be given a visibility tint to aid in its installation and positioning, for example, during surgery. For example, an optical tint (e.g. 'hawk-eye' style yellow-tint) may be used to enhance visual performance. For radiation safety, a UV-blocker may be added to the bulk material or surface coating of a SECL. In addition blue-blockers, tints for color-deficiencies, contrast enhancement tints, etc. and combinations thereof may be incorporated into the SECL. Alternatively, such additives may be incorporated into the liquid used to make the lens.

A mini-capsulorhexis valve (MCV) may be used during the phaco-ersatz operation without interference from the SECL. Conversely, the installation, positioning and operation of the SECL is designed not to be affected in a detrimental manner by the use of an MCV or other similar devices. The SECL itself may also be designed to act as a valve that operates in a similar manner to an MCV and/or to provide gel retention functionality. In addition, an access channel or port may be provided in the periphery of the SECL to permit manipulation of the portion of the MCV present within the capsule.

The SECL may also be designed with a built-in valve or some kind of gel retention system that operates in a similar manner to an MCV, thereby facilitating the injection of the phaco-ersatz polymer gel. Some possible options include in a simple case, a suitably located hole in the periphery of the SECL, or in the more involved design case, a small butterfly-type flap in the periphery to act as a valve. (See FIG. 2).

It is clear from the above description that given the variety of optical and mechanical features and strategies available to the SECL, the parameters of the SECL can range widely. However, Table 1 lists some preferred specifications for parameters of the SECL to provide guidance and illustration.

Table 1 sets forth specifications for preferred parameters of the SECL.

TABLE 1

| Parameter | Preferred Specification Range | More Preferred Specification Range | Most Preferred Specification Range |
| --- | --- | --- | --- |
| Overall (Haptic) Diameter[a] | 9.0 mm–10.5 mm | 9.5 mm–10 mm | Accommodated Diameter |
| Haptic Thickness | 0.01–0.1 mm | 0.01–0.05 mm | 0.01–0.02 mm |
| Optic Zone Size[b] | 4.5 mm–9.5 mm | 6.0 mm–9.0 mm | 7.5 mm–8.5 mm |
| Optics Young's Modulus[c] | 0.1 KPa–10 KPa | 0.5 Kpa–1 Kpa | Same as Polymer Gel |
| Haptic Young's Modulus | 0.1 KPa–20 KPa | 0.5 KPa–1.5 Kpa | Same as Polymer Gel |
| Optic Zone Refractive Index[d] | 1.2–1.8 | 1.3–1.75 | 1.33–1.67 |
| IR Transmission[e] | 80%–100% (1060 nm–1100 nm) | 80%–100% (1060 nm–1100 nm) | 85%–98% (1060 nm–1100 nm) |
| UV Transmission | <5% | <2% | <0.5% |

The upper limit of overall (or haptic) diameter range of the SECL is determined by the diameter of the accommodated crystalline lens. For some designs, allowance must be made for the decrease in equatorial diameter of the ersatz lens during accommodation. Furthermore, the design of the haptic and the intended antero-posterior location of the SECL would influence the choice of overall diameter. For example, if the SECL is to be positioned posteriorly, the overall diameter would need to be decreased to match the "equivalent" diameter of the accommodated lens at that axial depth.

The lower limit of optical zone size range of the SECL is determined by the pupil size of the patient. For example, older patients tend to have smaller pupil diameters even in dim light. Naturally, optical zone sizes may be customized according to the pupil size.

The SECL must be sufficiently flexible to be desirably compacted (e.g. rolled), and so as not to prevent mechanical accommodation of the ersatz lens. This defines the upper limit of the flexibility range of the SECL. While this factor des not impose a lower limit, the need to maintain some rigidity for either insertion or optical performance sets a lower limit to the flexibility of the SECL.

Refractive index preferred values apply only to the optic zone. The haptic zone need only be clear (although some amount of visibility tint may be introduced to facilitate implantation and alignment). Further, the refractive index to be selected for the SECL is dependent on the refractive index of the preferred polymer gel selected. As described earlier, the SECL may employ a more conventional higher-than-gel index approach for refraction, or make use of a lower-than-gel refractive index. The latter case has benefits particularly for the myopic eye. In addition, preferably, the infrared transmissibility of the SECL of the present invention is provided to permit retinal laser surgery.

Many preferred surgical techniques (phaco-ersatz) exist for restoring the accommodation of an eye by the injection of a suitable material into the capsule (such as those taught by Parel et al., 1981 & 1986, Haefliger et al., 1989 & 1994). However, according to such methods, while being able to restore the accommodative range of the eye, it has not been able to simultaneously correct for any ametropia (refractive error) of the eye.

Two strategies, as part of phaco-ersatz, have been touted as being able to correct ametropia: 1) being over or under-filling of the capsule, and 2) altering the refractive index of the injected material. However, when these techniques are employed to correct ametropia, they also alter the accommodative range afforded to the post-surgical eye.

The SECL of the present invention is a device that can be introduced during phaco-ersatz, which can correct ametropia while retaining a clinically useful amount of accommodation to the post-surgical eye. It achieves this by supplementing the static refractive power of the post-phaco-ersatz lens without compromising the dynamic refractive power (or accommodative range) of the lens. Currently, for ametropia correction to be effected without affecting accommodation with phaco-ersatz, the patient would need to resort to conventional devices such as spectacles or contact lenses, or an additional surgical procedure such as LASIK or PRK. However, the traditional forms of ametropia correction (spectacles, contact lenses) are not considered attractive by many patients due to their poor cosmesis, inconvenience of handling, and continued recurring costs of upkeep.

The more adventurous surgical techniques such as LASIK and PRK require additional surgery to be undertaken which necessitate a recovery period from phaco-ersatz before their application. Therefore, the patient will not attain full accommodation and correct ametropia in the one surgery. By contrast, the SECL is inserted during the same phaco-ersatz operation. Therefore, a second surgery and visit (and the additional risks associated) are unnecessary. The appropriate refractive power for correcting ametropia is provided by the SECL and is made available at the same time accommodative range is restored. The SECL provides the refractive power without unduly impacting the accommodative range made available through phaco-ersatz. In addition, since only a single surgical operation (phaco-ersatz itself) is needed, and the result is a permanent, no-maintenance device, the SECL is cost effective and maintenance-free compared to spectacles, contact lenses and laser refractive surgery, while exposing the patient to fewer potentially risky surgical operations.

While the primary purpose of phaco-ersatz or similar procedures is to restore accommodation in the presbyope, a large majority of such patients also possess significant refractive errors (ametropia) that requires correction. The phaco-ersatz or similar procedures by themselves, as discussed above, are not able to correct ametropia simultaneously without also affecting the range of accommodation delivered. Therefore, the application of a SECL by its introduction into the capsule of the crystalline lens during the phaco-ersatz operation would make the surgical procedure for restoring accommodation truly attractive to the ametropic presbyopic patient. In addition, the SECL is capable of simultaneously controlling optical aberrations (e.g. spherical aberrations) or modifying magnification or distortion to further enhance vision for the phaco-ersatz patient, for example, during surgical restoration of accommodation.

EXAMPLE 1

Method for Implantation of a SECL in the Lens Capsule and Lens Refilling Procedure (phaco-erzatz)

Dilation drops Mydriacyl 0.5% in the amount of 1 drop in each eye were added. Five (5) minutes later 1 drop in each was added of 1% atropine sulfate. The eye was then anesthetized with 35 mg/kg of ketamine and 5 mg/kg of xylazine with 0.75 mg/kg of acepromazine. After preparing the subject for surgery in aseptic conditions an eyelid speculum was inserted. A two step incision was made at the corneal periphery (1.5 mm in width). A mini-capsulorhexis was made (0.8–1.2 mm diameter). The lens material was aspirated. A cannula was then inserted (loaded with a pre-rolled SECL) through the mini-capsulorhexis into the lens capsule and disengaged from the cannula. The SECL then unfolded. A mini-capsulorhexis valve (MCV) was then placed across the capsule opening. A polymeric gel was then injected from a cannula through the capsulorhexis and into the lens capsule. When necessary, the gel was then crosslinked using an adequate light source and light source delivery fiber, and when applicable, the MCV was removed. The corneal wound was then closed with nylon 10–0 or 9–0. Neomycin and Polymixin B sulfate drops (1 drop) was placed onto the ocular surface of the eye.

EXAMPLE 2

In-Vitro Method for Verifying the Efficacy of a SECL in Correcting Ametropia Without Significantly Degrading the Accommodative Amplitude The instructions outlined in this Example present one method by which the optical efficacy of a SECL may be demonstrated in situ. It is understood that a wide range of optometric measurement methods may be used for the same purposes. The method described here is chosen as it involves only simple componentries.

A working SECL would typically have a diameter sufficiently large to cover the entire pupil of the eye in most illumination conditions. Further, individual eyes would differ in their amount of ametropia. Given these two constraints, it is extremely difficult and certainly impractical to demonstrate the difference in optical performance (refraction and accommodation) of a post-ersatz lens against a post-ersatz lens which also has had a SECL implant.

Therefore the simplest demonstration of a SECL's optical performance is by using a "reduced-diameter" SECL—one whose diameter has been reduced sufficiently to expose an area of an ersatz-lens which is covered by neither iris nor the SECL. Thus, this exposed area represents the optical performance of an ersatz lens without a SECL. The remainder of the lens would represent the optical performance of an ersatz lens with a SECL implant.

Optometers for measuring the refractive state of an eye make use of the entire, (or nearly the entire) pupil size of the eye. As such, it is difficult to measure separately the optical performance of the SECL, and the "exposed" area of an ersatz lens. Any measurement intended to demonstrate the difference between SECL and exposed ersatz lens area must be able to measure power across the pupil of the eye.

One such type of instrument are those making use of the Hartmann-Schack method. However, these instruments are relatively expensive and necessarily complex due to the need for "high end" components such as a micro-lenslet array. A less expensive and more straightforward demonstration of the efficacy of a SECL may be gained by an in vivo preparation using an animal eye model and transmission optometric measurements using a reduced-diameter SECL.

Procedure:

Select a suitable animal eye model (e.g. rabbit's eye).

Select a reduced-diameter SECL (RD-SECL) whose diameter is substantially less than the diameter of the crystalline lens (and preferably pupil diameter as well).

Conduct a phaco-ersatz procedure including the RD-SECL and MCV as described in the previous standard operating procedure.

Upon completion of the phaco-ersatz procedure, prepare the eye for mounting in a lens-stretcher apparatus such as described in Glasser & Campbell (Glasser A & Campbell M C. Presbyopia and the Optical Changes in the Human Crystalline Lens with Age. *Vision Research*. 1998 Volume 38, No. 2, pp. 209–229.), or Pierscionek et al (Pierscionek B K. In vitro alteration of human lens curvatures by radial stretching. *Experimental Eye Research* 1993, 57: 629–635, and Pierscionek B K. Age-related response of human lenses to stretching forces. *Experimental Eye Research* 1995, 60: 325–332), and removing the cornea, iris and all ocular tissues posterior to the equator of the eye (e.g. optic nerve, retina, posterior sclera, etc).

To the lens-stretcher apparatus, add an optometer system which is capable of measuring the power through different pupil locations (i.e. within the RD-SECL or outside the RD-SECL). One suitable system is shown in FIGS. 11–14. This system is based on the Foucault knife-edge principle commonly used in testing the figure of astronomical telescopes.

Figure 11:
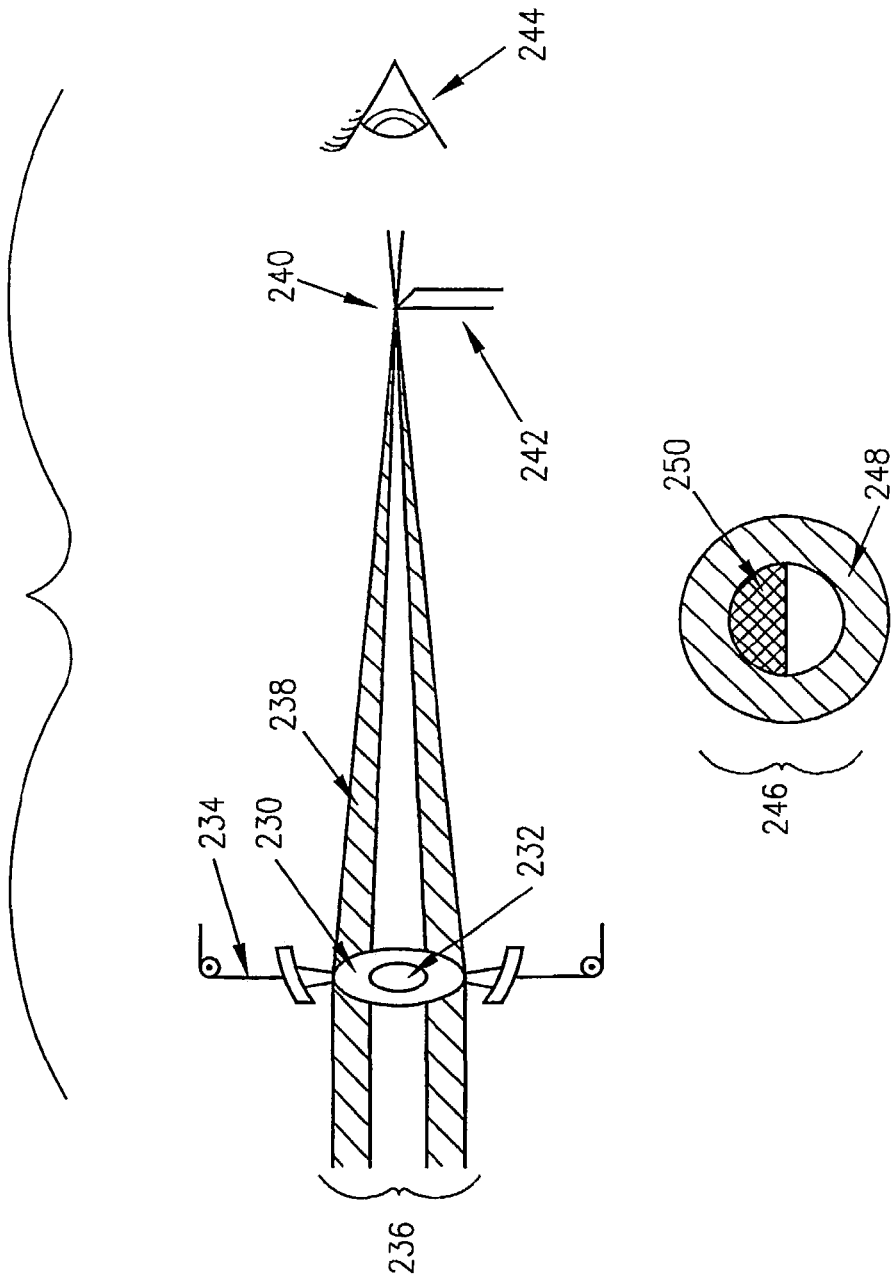

Demonstration of the optical performance of a lens with and without SECL is executed as follows and illustrated in FIGS. 11–14. Measurement of ersatz lens without a SECL and accommodation relaxed is shown in FIG. 11. The mounted ersatz lens 230 with the RD-SECL 232 is stretched to simulate relaxed accommodation by applying tension to the lens stretching system 234. Collimated (parallel) light 236 from the left is directed through the ersatz lens 230. The more peripheral light rays 238 will be directed through the portion of the ersatz lens 230 which is not covered by the RD-SECL. Hence, its focus 240 will represent the power of an accommodation-relaxed, ersatz lens without a SECL. This can be measured by placing a knife-edge 242 at the focal position 240 and observing the entire optical setup using a suitable observation system 244. The appearance through the observation system 244 when the knife-edge 242 is set to the focus 240 of the relaxed-accommodation, ersatz lens without a SECL is shown as 246 in which the outer pupillary region 248 marking the ersatz lens without a SECL will be seen as neutral (suggested by shading of 248). If the RD-SECL 232 has a positive power (for correcting hypermetropia) as in this example, then the appearance 246 through the observation system 244 will be an inner region 250 marking the ersatz lens with the RD-SECL 232 having a dark upper field and a bright lower field indicating relatively positive power. The reciprocal of the distance from the focus 240 to the ersatz lens 230 is the power of the relaxed ersatz lens without a SECL. We shall call this quantity F1.

Figure 12:
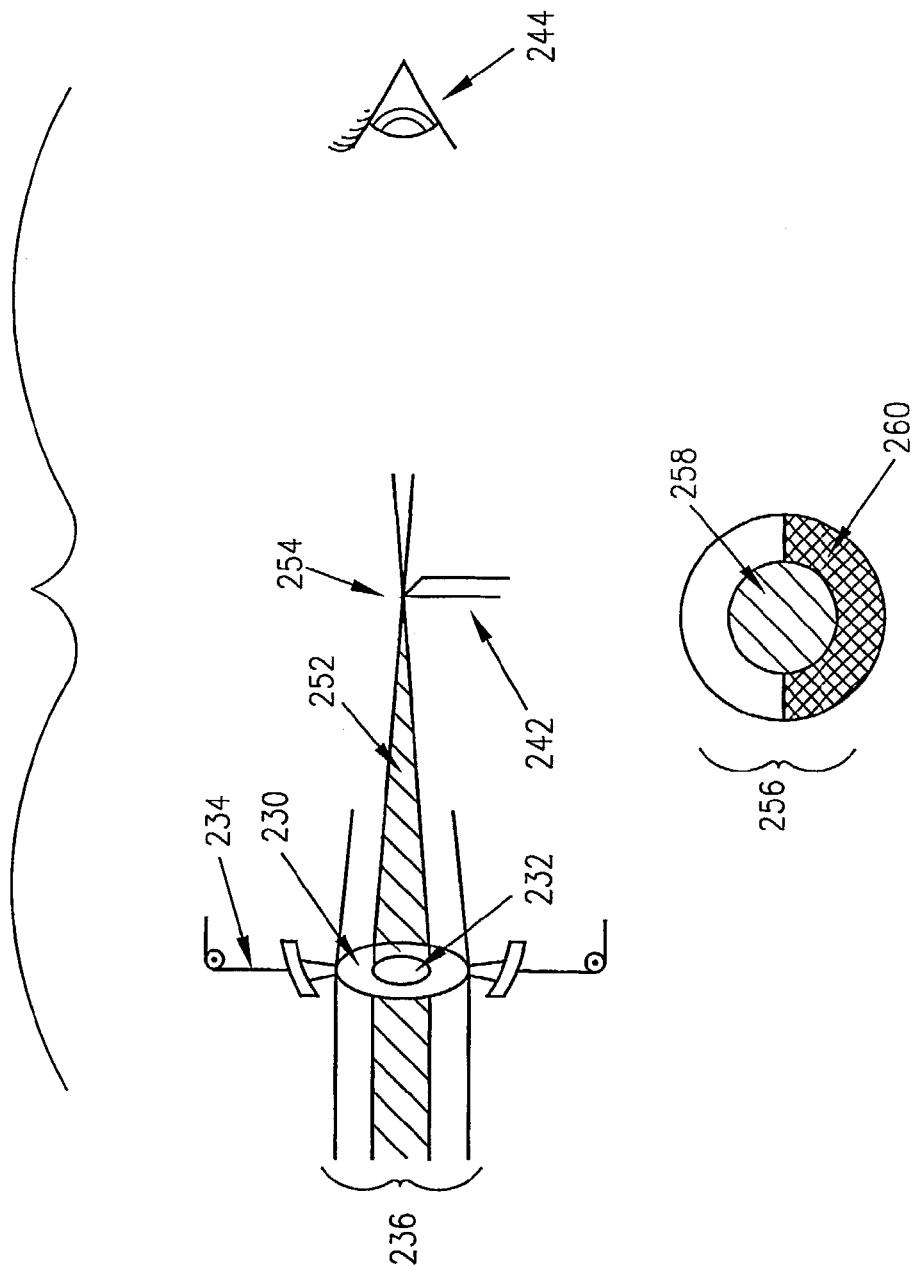

Measurement of ersatz lens with a SECL and accommodation relaxed is shown in FIG. 12. The mounted ersatz lens 230 with the RD-SECL 232 is stretched to simulate relaxed accommodation by applying tension to the lens stretching system 234. Collimated (parallel) light 236 from the left is directed through the ersatz lens 230. The more central light rays 252 will be directed through the portion of the ersatz lens 230 which includes the RD-SECL 232. Hence, its focus 254 will represent the power of an accommodation-relaxed, ersatz lens including a SECL. This can be measured by placing a knife-edge 242 at the focal position 254 and observing the entire optical setup using a suitable observation system 244. The appearance through the observation system 244 when the knife-edge 242 is set to the focus 254 of the relaxed-accommodation, ersatz lens with a SECL is shown as 256 in which the central pupillary region 258 marking the ersatz lens with a SECL will be seen as neutral (suggested by shading of 258). If the RD-SECL 232 has a positive power (for correcting hypermetropia) as in this example, then the appearance through the observation system 244 will be an outer/peripheral region 260 marking the ersatz lens without a SECL having a dark lower field and a bright upper field indicating relatively negative power. The reciprocal of the distance from the focus 254 to the ersatz lens 230 is the power of the relaxed ersatz lens with a SECL.

We shall call this quantity F2.

Measurement of ersatz lens without a SECL and accommodation exerted is shown in FIG. 13. The mounted ersatz lens 230 with the RD-SECL 232 is allowed to relax to simulate activated accommodation by removing tension from the lens stretching system 234. Collimated (parallel) light 236 from the left is directed through the ersatz lens 230. The more peripheral light rays 238 will be directed through the portion of the ersatz lens 230 which is not covered by the RD-SECL. Hence, its focus 262 will represent the power of an accommodated ersatz lens without a SECL. This can be measured by placing a knife-edge 242 at the focal position 262 and observing the entire optical setup using a suitable observation system 244. The appearance through the observation system 244 when the knife-edge 242 is set to the focus 262 of the accommodated ersatz lens without a SECL is shown as 246 in which the outer pupillary region 248 marking the ersatz lens without a SECL will be seen as neutral (suggested by shading of 248). If the RD-SECL 232 has a positive power (for correcting hypermetropia) as in this example, then the appearance through the observation system 246 will be an inner region 250 marking the ersatz lens with the RD-SECL 232 having a dark upper field and a bright lower field indicating relatively positive power. The reciprocal of the distance from the focus 262 to the ersatz lens 230 is the power of the accommodated ersatz lens without a SECL. We shall call this quantity F3.

Measurement of ersatz lens with a SECL and accommodation exerted is shown in FIG. 14. The mounted ersatz lens 230 with the RD-SECL 232 is allowed to relax to simulate activated accommodation by removing tension from the lens stretching system 234. Collimated (parallel) light 236 from the left is directed through the ersatz lens 230. The more central light rays 252 will be directed through the portion of the ersatz lens 230 which includes the RD-SECL 232. Hence, its focus 264 will represent the power of an accommodated ersatz lens including a SECL. This can be measured by placing a knife-edge 242 at the focal position 264 and observing the entire optical setup using a suitable observation system 244. The appearance through the observation system 244 when the knife-edge 242 is set to the focus 264 of the accommodated ersatz lens with a SECL is shown as 256 in which the central pupillary region 258 marking the ersatz lens with a SECL will be seen as neutral (suggested by shading of 258). If the RD-SECL 232 has a positive power (for correcting hypermetropia) as in this example, then the appearance through the observation system 246 will be an outer/peripheral region 260 marking the ersatz lens without a SECL having a dark lower field and a bright upper field indicating relatively negative power. The reciprocal of the distance from the focus 264 to the ersatz lens 230 is the power of the accommodated ersatz lens with a SECL. We shall call this quantity F4.

By conducting the above measurements, it can be demonstrated that F2 will differ from F1 by a similar amount to F4 and F3 thus showing that the SECL provides a measurable difference in the refractive power of the ersatz lens with a SECL and hence is capable of correcting ametropia. It can also be demonstrated that the differences F4−F2 and F3−F1 will be approximately similar thereby indicating that the amplitude of accommodation is not affected by the application of a SECL.

While the present invention has been described with respect to specific examples, it will be apparent to those of ordinary skill in the field that the invention is not limited to these specific examples and embodiments but extends to other embodiments as well. The present invention therefore includes all of these other embodiments as specified in the claims that follow.

What is claimed is:

1. A method of simultaneously supplementing refractive power of an eye and increasing accommodative capacity of an eye comprising the steps of:
    performing a phaco-ersatz procedure to remove a lens from the lens capsule of an eye;
    introducing a polymer into the lens capsule;
    inserting a compacted supplementary endo-capsular lens into the lens capsule, said supplementary endo-capsular lens made from a material having a refractive index that is not equal to the refractive index of the polymer; and
    positioning the supplementary endo-capsular lens in the lens capsule.

2. The method according to claim 1, wherein a capsulorhexis is made in the lens capsule in the step of performing a phaco-ersatz procedure, through which the lens is removed, the polymer is introduced, and the supplementary endo-capsular lens is inserted.

3. The method according to claim 1, wherein the steps of inserting and positioning the supplementary endo-capsular lens in the lens occurs prior to the step of introducing a polymer into the lens capsule.

4. The method according to claim 1, further comprising the step of curing the polymer.

5. The method according to claim 1, wherein the steps of inserting and positioning the supplementary endo-capsular lens in the lens occurs prior to the step of introducing a polymer into the lens capsule.

6. The method according to claim 1, wherein the polymer is a polymer gel.

7. The method according to claim 1, wherein the polymer gel is made from a material selected from the group consisting of siloxanes, hydrogels and combinations thereof.

8. The method according to claim 1, wherein the supplementary endo-capsular lens is made from a material selected from the group consisting of polymethylphenylsiloxane, polyfluoropropylmethylsiloxane, hydroxyethyl methacrylate, methyl methacrylate, ethyl methacrylate, phenylethylacrylate, phenylethylmethylacrylate and combinations thereof.

9. The method according to claim 1, wherein the capsulorhexis has a diameter of less than about 1 mm.

10. The method according to claim 1, wherein the supplementary endo-capsular lens, is in a rolled orientation.

11. The method according to claim 1, wherein the supplementary endo-capsular lens is in a rolled orientation.

12. The method according to claim 1, wherein the supplementary endo-capsular lens is made from a material having a lower refractive index than the refractive index of the polymer.

13. The method according to claim 1, wherein the supplementary endo-capsular lens is made from a material having a higher refractive index than the refractive index of the polymer.

14. The method according to claim 1, wherein the in situ refractive effect of the supplementary endo-capsular lens is equal and opposite to the ametropia of an eye into which the supplementary endo-capsular lens is implanted.

15. The method according to claim 1, wherein the supplementary endo-capsular lens and the cured polymeric gel lens combine to produce emmetropia without significantly impairing accommodation.

16. The method according to claim 1, wherein the supplementary endo-capsular lens has an integrated aberration control.

17. The method according to claim 16, wherein the aberration control can he predictably altered to affect accommodation.

18. The method according to claim 1, wherein the s upplementary endo-capsular lens has a predetermined degree of magnification.

19. The method according to claim 1, wherein the supplementary endo-capsular lens is made from a material having a specific gravity of from about 0.9 to about 1.5.

20. The method according to claim 19, wherein the specific gravity of the supplementary endo-capsular lens assists in the positioning of the supplementary endo-capsular lens in the lens capsule.

21. The method according to claim 1, wherein the supplementary endo-capsular lens has a specific gravity that is higher than the specific gravity of the polymer.

22. The method according to claim 1, wherein the supplementary endo-capsular lens has a specific gravity that is lower than the specific gravity of the polymer.

23. The method according to claim 1, wherein the polymer has a specific gravity of from about 0.9 to about 1.5.

24. The method according to claim 1, wherein the supplementary endo-capsular lens has integral alignment features.

25. The method according to claim 24, wherein the integral alignment features comprise indicia.

26. The method according to claim 1, wherein the supplementary endo-capsular lens comprises a hap tic.

27. The method according to claim 1, wherein the supplementary endo-capsular lens comprises additional components selected from the group consisting of tints, UV blockers, blue blockers, color deficiency agents, contrast-enhancing agents and combinations thereof.

28. The method according to claim 1 wherein the polymer comprises additional components selected from the group consisting of tints, UV blockers, blue blockers, color deficiency agents, contrast-enhancing agents and combinations thereof.

29. The method according to claim 1, wherein the supplementary endo-capsular lens can correct vision in a range of from about −20 diopters to about 20 diopters.

30. A method of simultaneously supplementing refractive power of an eye and increasing accommodative capacity of an eye comprising the steps of
performing a phaco-ersatz procedure to remove a lens from the lens capsule of an eye through a capsulorhexis;
introducing a polymer into the lens capsule through the capsulorhexis;
inserting a compacted supplementary endo-capsular lens into the lens capsule through the capsulorhexis, said supplementary endo-capsular lens made from a material having a refractive index that is not equal to the refractive index of the polymer; and
positioning the supplementary endo-capsular lens in the lens capsule.

31. The method according to claim 30, further comprising the step of curing the polymer.

32. A method of simultaneously supplementing refractive power of an eye and increasing accommodative capacity of an eye comprising the steps of:
performing a phaco-ersatz procedure to remove a lens from the lens capsule of au eye through a capsulorhexis;
introducing a polymer gel into the lens capsule through the capuslorhexis, said polymer gel made from a material selected from the group consisting of siloxanes, hydrogels and combinations thereof;
inserting a supplementary endo-capsular lens into the lens capsule through the capsulorhexis, said supplementary endo-capsular lens made from a material having a refractive index that is not equal to the refractive index of the polymer, said material selected from the group consisting of polymethylphenylsiloxane, polyfluoropropylmethylsiloxane, hydroxyethyl methacrylate, methyl methacrylate, ethyl methacrylate, phenylethylacrylate, phenylethylmethylacrylate and combinations thereof;
positioning the supplementary endo-capsular lens in the lens capsule; and
curing the polymer gel.

33. The method according to claim 32, wherein the steps of inserting and positioning the supplementary endo-capsular lens in the lens capsule occur prior to the step of introducing the polymer gel into the lens capsule.

34. A device for simultaneously supplementing refractive power of an eye and increasing accommodative capacity of an eye comprising an amount of fluid introduced into a substantially empty lens capsule of an eye, and a compacted supplementary endo-capsular lens introduced into the lens capsule through the capsulorhexis and positioned in situ in the fluid, after which, the fluid is cured to achieve the desired refractive power and accommodative capacity.

35. The device according to claim 34, wherein the fluid introduced into the lens capsule is cured after the supplementary endo-capsular lens is positioned in the lens capsule.

36. The device according to claim 34, wherein the fluid is-introduced through a capsulorhexis in the lens capsule, and the supplementary endo-capsular lens is introduced into the lens capsule through the capsulorhexis.

37. The device according to claim 34, wherein the specific gravity of the fluid is from about 0.9 to about 1.5.

38. The device according to claim 34, wherein the supplementary endo-capsular lens has integral alignment features.

39. The device according to claim 38, wherein the integral alignment features arc integral indicia.

40. The device according to claim 34, wherein the supplementary endo-capsular lens comprises a haptic.

41. The device according to claim 34, wherein the supplementary endo-capsular lens comprises additional components.

42. The device according to claim 41 wherein the additional components are selected from the group consisting of tints, UV blockers, blue blockers, color deficiency agents, contract enhancement tints, and combinations thereof.

43. The device according to claim 34, wherein the supplementary endo-capsular lens is convex.

44. The device according to claim 34, wherein the supplementary endo-capsular lens can correct vision in a range of from about −20 diopters to about 20 diopters.

45. A device for simultaneously supplementing refractive power of an eye and increasing accommodative capacity of an eye comprising an amount of polymer inserted into an empty lens capsule of an eye, and a supplementary endo-capsular lens made from a material having a refractive index that is not equal to the refractive index of the polymer, said supplementary end-capsular lens positioned in situ in the polymer to achieve the desired refractive power and accommodative capacity.

46. The device according to claim 45, wherein the polymer is cured.

47. The device according to claim 46, wherein the supplementary endo-capsular lens and the cured polymer combine to produce emmetropia without significantly impairing accommodation.

48. The device according to claim 45, wherein the polymer is a polymer gel.

49. The device according to claim 45, wherein the polymer is introduced through a capsulorhexis in the lens capsule, and the supplementary endo-capsular lens is introduced into the lens capsule through the capsulorhexis.

50. The device according to claim 45, wherein the polymer is made from a material selected from the group consisting of siloxanes, hydrogels and combinations thereof.

51. The device according to claim 45, wherein the supplementary endo-capsular lens is made from a material selected from the group consisting of polymethylphenylsiloxane, polyfluoropropylmethylsiloxane, hydroxyethyl methacrylate, methyl methacrylate, ethyl methacrylate, phenylethylacrylate, phenylethylmethylacrylate and combinations thereof.

52. The device according to claim 45, wherein the supplementary endo-capsular lens is made from a material having a lower refractive index than the refractive index of the polymer.

53. The device according to claim 45, wherein the supplementary endo-capsular lens is made from a material having a higher refractive index than the refractive index of the polymer.

54. The device according to claim 45, wherein the in situ refractive effect of the supplementary endo-capsular lens, is equal and opposite to the ametropia of an eye into which the supplementary endo-capsular lens is implanted.

55. The device according to claim 45, wherein the supplementary endo-capsular lens has an integrated aberration control.

56. The device according to claim 55, wherein the aberration control can be predictably altered to affect accommodation.

57. The device according to claim 45, wherein the supplementary endo-capsular lens has a predetermined degree of magnification.

58. The device according to claim 45, wherein the supplementary endo-capsular lens is made from a material having a specific gravity of from about 0.9 to about 1.5.

59. The device according to claim 58, wherein the specific gravity of the supplementary endo-capsular lens assists in the positioning of the supplementary endo-capsular lens in the lens capsule.

60. The device according to claim 45, wherein the specific gravity of the supplementary endo-capsular lens is higher than the specific gravity of the polymer.

61. The device according to claim 45, wherein the specific gravity of the supplementary endo-capsular lens is lower than the specific gravity of the polymer.

62. A device for simultaneously supplementing refractive power of an eye and increasing accommodative capacity of an eye comprising:
   a polymer gel injected into an evacuated lens capsule through a capsulorhexis, said polymer gel made from a material selected from the group consisting of siloxanes, hydrogels, and combinations thereof; and
   a supplementary endo-capsular lens inserted through the capsulorhexis into the lens capsule and positioned within the polymer gel, said supplementary endo-capsular lens having a refractive index that is not equal to the refractive index of the polymer gel, said supplementary end-capsular lens made from a material selected from the group consisting of polymethyiphenylsiloxane, polyfluoropropylmethylsiloxane, hydroxyethyl methacrylate, methyl methacrylate, ethyl methacrylate, phenylethylacrylate, phenylethylmethylacrylate and combinations thereof.

* * * * *